United States Patent [19]
Andrews et al.
[11] Patent Number: 4,874,705
[45] Date of Patent: Oct. 17, 1989

[54] DNA ENCODING AN ANTIGENIC PROTEIN DERIVED FROM *EIMERIA TENELLA* AND VACCINES FOR PREVENTION OF COCCIDIOSIS CAUSED BY *EIMERIA TENELLA*

[75] Inventors: William H. Andrews, Belmont; Virginia M. Brothers, Albany; James G. Files, Belmont; Irene Kuhn, San Francisco; Michael T. McCaman, San Bruno; Leland S. Paul, Woodside; Stacey R. Sias, San Anselmo, all of Calif.; Thomas C. Gore, Charles City; Karel Z. Newman, Jr., Clear Lake, both of Iowa; John L. Tedesco, St. Peters, Mo.

[73] Assignee: Solvay & Cie, S.A., Brussels, Belgium

[21] Appl. No.: 805,824

[22] Filed: Dec. 6, 1985

Related U.S. Application Data

[63] Continuation-in-part of Ser. No. 734,085, May 16, 1985, which is a continuation-in-part of Ser. No. 617,483, Jun. 5, 1984, abandoned.

[51] Int. Cl.$^4$ .................... C12N 1/20; C12N 15/00; C07H 21/04

[52] U.S. Cl. .................... 435/252.33; 435/68; 435/320; 536/27; 424/88; 530/806; 530/350

[58] Field of Search .................... 435/68, 320, 172.3, 435/253; 536/27; 424/88

[56] References Cited

U.S. PATENT DOCUMENTS

| | | | |
|---|---|---|---|
| 4,639,372 | 1/1987 | Murray et al. | 530/403 |
| 4,650,676 | 3/1987 | Schenkel et al. | 424/88 |
| 4,710,377 | 12/1987 | Schenkel et al. | 424/88 |

FOREIGN PATENT DOCUMENTS

| | | |
|---|---|---|
| 167443 | 1/1986 | European Pat. Off. . |
| 231537 | 8/1987 | European Pat. Off. . |
| 8600528 | 1/1986 | PCT Int'l Appl. . |

*Primary Examiner*—Blondel Hazel
*Attorney, Agent, or Firm*—John P. White

[57] ABSTRACT

A genomic DNA molecule having the nucleic acid sequence set forth in FIG. 1 and encoding an antigenic protein derived from *Eimeria tenella* has been isolated. The protein has a molecular weight of about 25,000 daltons and is composed of two polypeptides joined by a disulfide bond. One of the polypeptides is characterized by a molecular weight of about 17,000 daltons and by a blocked N-terminal amino acid and having the amino acid sequence set forth in FIG. 1. The other polypeptide is characterized by a molecular weight of about 8,000 daltons and has the amino acid sequence set forth in FIG. 1.

A cDNA molecule encoding the 25,000 dalton polypeptide with a continuous amino acid sequence has been inserted into expression vectors capable of expressing the 25,000 dalton polypeptide directly or as a fused polypeptide. The polypeptides produced are used in vaccines to immunize chickens against infection by *Eimeria tenella.*

26 Claims, 14 Drawing Sheets

FIG. 1a

```
                                                 AGATCTATCAAGCAATAATCATCTA
CCTCCAAATATATGCTATGAAATGC7AAATT8CGTCAGAGTGATTCGTCACAGCAACGTC
TCATGCAGAGTGCCCGAGAACTGA5GGGAGAAACAGTGGAGTGACCGCGGGTCGCTGGTA
TTTTCTTGCTTTCATTOGCAAACGYGGCATTTTCAAGTGCCATTTTTCTTGTAATCACAT
TAGTTTGCCAGTAAATGAGGGGAATATTCTGGTGTAAGCTGTTCTTCTGGCAGTTTCACG
AGAGTCACACCGTCACCTGGOAGGTAACCTGGAAAGGGGCGGTGGCAGGAATGGCGCAAG
GCATGGAACAATGAAAGCTGAGAGCAGCGTCAAA3GGATGAATTTTCAATTTCACGTTTG
CCCTTAAATCCATTCAAGTGGGCCGAGACCGCTCTCGGAAGYGCAGTCTCGTTTGCGATT
GCATTMCCTGCACACACCTATGACGACGTACGGTGTTGGGCAGAACCTGAACATAGCGTT
TACGTCTAMAGCCGCAGCCCAAAGAAACTCTGCATACTTTTGCCAAGATATTTCAAATAA
AACCTCTTTGCCGAATTGTATTTTCACCCTCTATCTACTATTTCCTGCCCACTATGAGAG
GCAGCAAGC7GTAGCGTGCCTTCCAATGGCCAGCACCAGCGCGCCAG7TAGGGCAGCAGC
TGTCAACCTCGCTGTCATCTGTCAACAGGCCGCCAGAACTCTTCCCATATCTGTCAAAAC
ATATTTATCTGCTCACTTTACAGTTTCTGTACAGTCACTTTTGCATATTATACAATTACT

                         MetAlaArgLeuSerPheValSerLeuLeuSerLeuSer
GTACAGTCATATTTGCTCAAAATGGCTCGTCTTTCTTTTGTTTCTCTTCTTTCTCTGTCA

                                              *
LeuLeuPheGlyGlnGlnAlaValArgAlaGlnAspTyrProThrAlaV<----------
CTGCTCTTCGGGCAGCAAGCAGTCAGAGCTCAGGATTACCCAACAGCAGGTGGGCTTTTC
                         SacI

------------------Intron A---------------------------------
CGCTAGCTGTTTTTGGTCCGATAGCATCGGAGCATCTCCCAAAACGAGGTGCATTCACC

------------------------------->alThrLeuAspCysLysGluAlaMetAsn
TTTTGCATGTTGTGTGCGGAAATTTTATCAGTTACGCTGGACTGTAAAGAAGCGATGAAC

LysLeuArgLysAlaAlaGlyLeuProAlaPheGluAspAlaValGlyAspThrPheVal
AAGCTGAGAAAAGCAGCAGGACTTCCTGCATTCGAAGATGCTGTGGGAGACACATTTGTT

LeuProAlaTyrSerHisGluGluSerArgAlaAlaProValAlaGluThrLeuTrpLys
CTACCAGCATACTCGCATGAAGAGTCTAGGGCGGCACCAGTAGCTGAAACTCTCTGGAAG

ThrGluIleCysProLysValLeuGly<-------------------------------
ACGGAGATATGCCCCAAAGTCTTAGGAGTAAGCCGTCCACGGCCTTGCATCGTCATGATG
```

FIG. 1

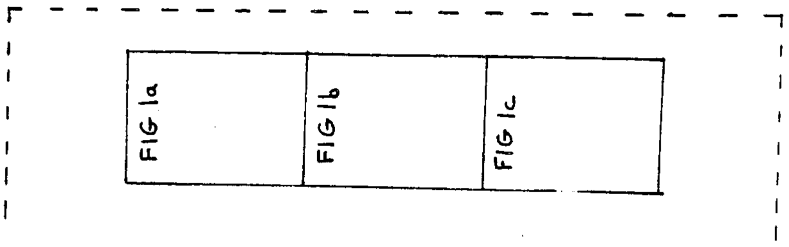

Figure 1b

```
--------------------Intron B---------------------------------
TAGTAGGTGTTCTGAGCAGCTTCGTTCTGTGGAACAAGGAACTACACTGTCCTTGAATTT

-------------------->GlyGlyArgSerArgAsnValThrGluAlaValLysLeu
TTAATCTTTTGTTACGTACAGGGCGGAAGGTCCAGGAACGTTACTGAAGCTGTCAAGTTA

ThrGlyAsnPheAlaTyrTyrProValThrAspGlyLysLysGluCysSerAspAlaVal
ACTGGCAATTTTGCCTACTACCCCGTCACAGACGGCAAAAAAGAGTGCAGCGATGCTGTG

GluTyrTrpLysGlyGlyLeuSerGlnPheAsnAspThrIleProProThrPheGlnAla
GAGTACTGGAAAGGCGGACTTTCTCAGTTCAACGACACAATTCCCCCAACGTTCCAAGCG

LeuAsnAspProValValTyrAsnAspArgAlaValSerPheValAlaLeuTyrAsnPro
TTGAACGACCCCGTTGTGTACAATGACAGGGCTGTTTCCTTTGTCGCCCTATACAACCCC

                                                          **
LysThrSerProValValSerCysValLeuLeuGlnCysProAsnAlaGlyValGlyGly
AAAACCAGCCCCGTTGTCAGTTGCGTGCTCCTCCAGTGCCCTAATGCAGGTGTTGGTGGA

            *
ArgArgLeuAlaAlaGlyThrThrAspAlaValIleCysLeuThrAsnProAlaProLeu
CGCAGGCTTGCGGCAGGCACGACAGACGCTGTCATTTGCTTGACAAATCCGGCTCCTTTG

GluAlaArgSerGlnProPheAs<------------------------------------
GAAGCAAGGTCACAACCATTCGAGTGAGAGTCAGCTGGTCGCCACTGCAACATGCATCAA
                               PvuII

---------------------Intron C-------------------------------
TGCGGCAGGTTACACTGGGGGTC7TGAGGTTGGTTGAAGCGCAATCTTCTAATACTTGTT

-------------------------->pAspGluGlnTrpLysLysIleValAspSerLe
TGTAATGTTTGTAATGTTTGCGTGCAGCGACGAGCAATGGAAGAAAATTGTTGACTCTCT

uSerLeuSerGluGluGluGluGluLysGlyGlyValSerProValValProSerValAl
ATCTCTCTCTGAGGAAGAGGAAGAGAAGGGCGGAGTTTCTCCAGTCGTCCCTTCAGTAGC

                                          **
aLeuIleSerAlaAlaValIleSerAlaPheAlaLeuPhe
CCTCATCTCTGCGGCGGTCATCTCCGCTTTCGCTCTCTTTTAGGCGGGCGCCGGTTGTTA

GTGACACACCAGCATTGGACAGATATGGCGGCGCAAGTTCCTTCCTGAGTGAAATCCTTG

AGTGACAAACGAGCACCTCTCCTGGACGAAATGTGATGAATTAAGACAGCTTTGGTTGTT

TGAAGTGTATGCAAAAGCTACATTTGTAGGGCCCTTTTATAGGATAATCGGAGGAAGCGC

AATTTTATTTAAAACCCTTGCAGAGAGTCGCCACGTGCGAGTGCAAGTGTTGCGCAGTGT

GTGCTGCCAAATGAAATTCTCGATCTTTAGTGTACTCAAGCCAGAAGTTTCGGCGTTGAT

GTACCCGCCGGTGGTATCTGCCATGCCATGCCTGCCTGTTTGGGCAGTACAACCTCATAC
```

Figure 1c

CAAGTGGCTTGTGTCATGGCATGTGTGGCCAAGCTACTTTTAGAGGGACAACAATGGGGA
TATTTTGAAGTATTTCGGATAAATACTCATCTGCTGTCCCTACCCACTGAGGCGCCATGG
TGTTACCTTCCTCATTTGAAGGGGAAAACTTGGTTGATAATTTCTTGTCCTTCAACTTGT
CTTGATAAATCGAAGATTATATTGTAGATAGTATACGTGGTGAACAGTTTTTAGGGAAGA
CTGTAAACCACAAGTTAAACGTAGTCGGAATTC

Legend

° Initial amino acid of 17,000 dalton peptide
°° Final amino acid of 17,000 dalton peptide
+ Initial amino acid of 8,000 dalton peptide
++ Final amino acid of 8,000 dalton peptide Key to ambiguous bases 3 = Probably C
5 = Probably A
7 = Maybe C
8 = Maybe T
0 = Maybe G
Y = C or T
M = C or G

FIG. 4

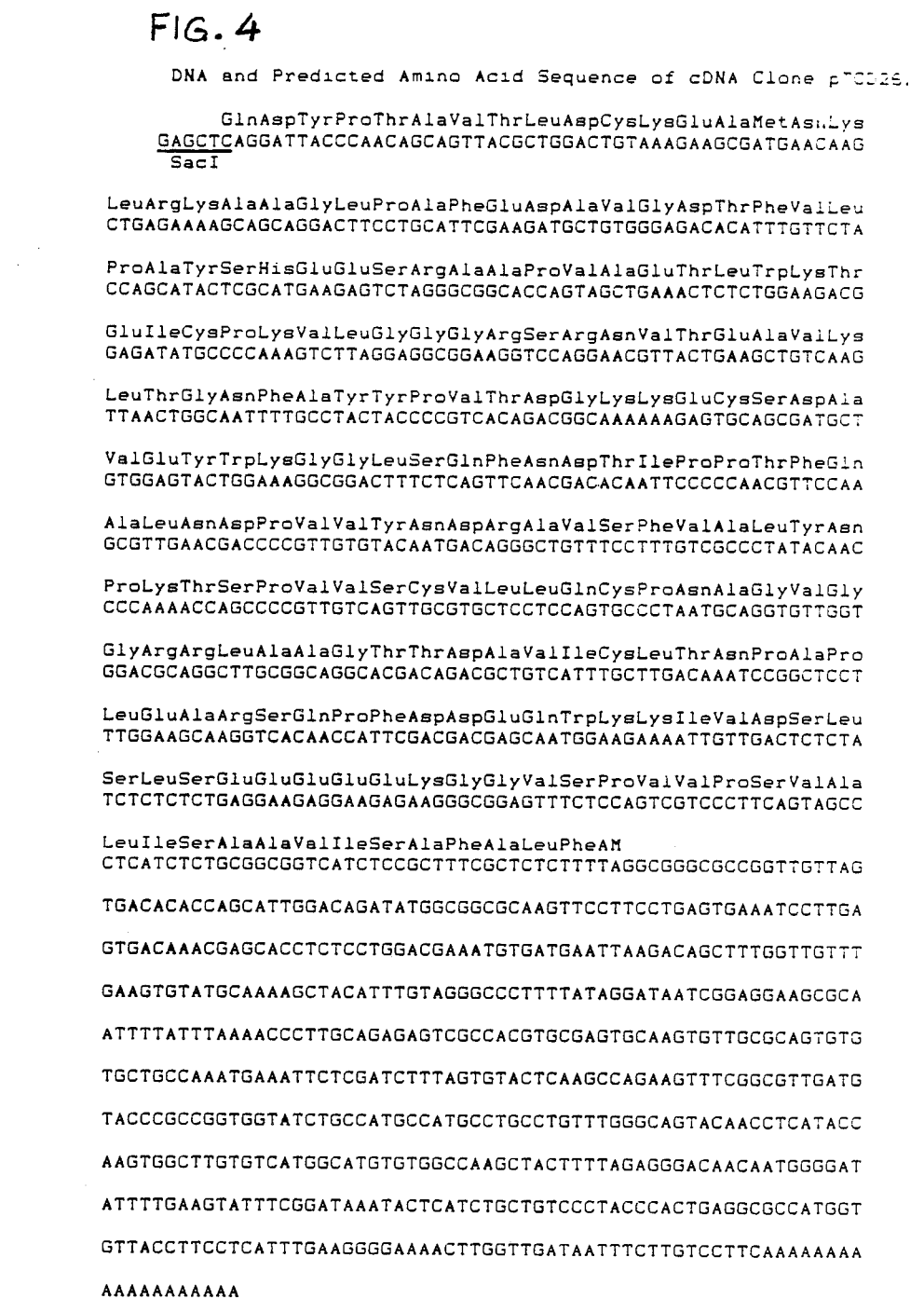

DNA and Predicted Amino Acid Sequence of cDNA Clone p[illegible].

```
     GlnAspTyrProThrAlaValThrLeuAspCysLysGluAlaMetAsnLys
  GAGCTCAGGATTACCCAACAGCAGTTACGCTGGACTGTAAAGAAGCGATGAACAAG
   SacI

LeuArgLysAlaAlaGlyLeuProAlaPheGluAspAlaValGlyAspThrPheValLeu
CTGAGAAAAGCAGCAGGACTTCCTGCATTCGAAGATGCTGTGGGAGACACATTTGTTCTA

ProAlaTyrSerHisGluGluSerArgAlaAlaProValAlaGluThrLeuTrpLysThr
CCAGCATACTCGCATGAAGAGTCTAGGGCGGCACCAGTAGCTGAAACTCTCTGGAAGACG

GluIleCysProLysValLeuGlyGlyGlyArgSerArgAsnValThrGluAlaValLys
GAGATATGCCCCAAAGTCTTAGGAGGCGGAAGGTCCAGGAACGTTACTGAAGCTGTCAAG

LeuThrGlyAsnPheAlaTyrTyrProValThrAspGlyLysLysGluCysSerAspAla
TTAACTGGCAATTTTGCCTACTACCCCGTCACAGACGGCAAAAAAGAGTGCAGCGATGCT

ValGluTyrTrpLysGlyGlyLeuSerGlnPheAsnAspThrIleProProThrPheGln
GTGGAGTACTGGAAAGGCGGACTTTCTCAGTTCAACGACACAATTCCCCCAACGTTCCAA

AlaLeuAsnAspProValValTyrAsnAspArgAlaValSerPheValAlaLeuTyrAsn
GCGTTGAACGACCCCGTTGTGTACAATGACAGGGCTGTTTCCTTTGTCGCCCTATACAAC

ProLysThrSerProValValSerCysValLeuLeuGlnCysProAsnAlaGlyValGly
CCCAAAACCAGCCCCGTTGTCAGTTGCGTGCTCCTCCAGTGCCCTAATGCAGGTGTTGGT

GlyArgArgLeuAlaAlaGlyThrThrAspAlaValIleCysLeuThrAsnProAlaPro
GGACGCAGGCTTGCGGCAGGCACGACAGACGCTGTCATTTGCTTGACAAATCCGGCTCCT

LeuGluAlaArgSerGlnProPheAspAspGluGlnTrpLysLysIleValAspSerLeu
TTGGAAGCAAGGTCACAACCATTCGACGACGAGCAATGGAAGAAAATTGTTGACTCTCTA

SerLeuSerGluGluGluGluGluLysGlyGlyValSerProValValProSerValAla
TCTCTCTCTGAGGAAGAGGAAGAGAAGGGCGGAGTTTCTCCAGTCGTCCCTTCAGTAGCC

LeuIleSerAlaAlaValIleSerAlaPheAlaLeuPheAM
CTCATCTCTGCGGCGGTCATCTCCGCTTTCGCTCTCTTTTAGGCGGGCGCCGGTTGTTAG

TGACACACCAGCATTGGACAGATATGGCGGCGCAAGTTCCTTCCTGAGTGAAATCCTTGA

GTGACAAACGAGCACCTCTCCTGGACGAAATGTGATGAATTAAGACAGCTTTGGTTGTTT

GAAGTGTATGCAAAAGCTACATTTGTAGGGCCCTTTTATAGGATAATCGGAGGAAGCGCA

ATTTTATTTAAAACCCTTGCAGAGAGTCGCCACGTGCGAGTGCAAGTGTTGCGCAGTGTG

TGCTGCCAAATGAAATTCTCGATCTTTAGTGTACTCAAGCCAGAAGTTTCGGCGTTGATG

TACCCGCCGGTGGTATCTGCCATGCCATGCCTGCCTGTTTGGGCAGTACAACCTCATACC

AAGTGGCTTGTGTCATGGCATGTGTGGCCAAGCTACTTTTAGAGGGACAACAATGGGGAT

ATTTTGAAGTATTTCGGATAAATACTCATCTGCTGTCCCTACCCACTGAGGCGCCATGGT

GTTACCTTCCTCATTTGAAGGGGAAAACTTGGTTGATAATTTCTTGTCCTTCAAAAAAAA

AAAAAAAAAAA
```

. Analysis of pDET1 and pDET2 proteins

A. Stained gel, pDET1

B. Immunoblot, pDET1

C. Stained gel, pDET2

Analysis of pBGC23 protein
A. Stained gel
B. Immunoblot

. Analysis of pCOC12 and pCOC20 proteins

A. Stained gel, pCOC12
B. Immunoblot, pCOC12
C. Stained gel, pCOC20

Immunoreactivity (ELISA) of TA4 antigen and renatured TA4 proteins with monoclonal antibody Ptn7.2 A4/4

DNA ENCODING AN ANTIGENIC PROTEIN DERIVED FROM *EIMERIA TENELLA* AND VACCINES FOR PREVENTION OF COCCIDIOSIS CAUSED BY *EIMERIA TENELLA*

BACKGROUND OF THE INVENTION

This application is a continuation-in-part of U.S. Ser. No. 734,085, filed May 16, 1985, which is a continuation-in-part of U.S. Ser. No. 617,483, filed June 5, 1984, now abandoned, the contents of both of which are hereby incorporated by reference.

Throughout this application, various publications are referenced by Arabic numerals within parentheses. Full citations for these references may be found at the end of the specification immediately preceding the claims. The disclosures of these publications in their entireties are hereby incorporated by reference into this application in order to more fully describe the state of the art as known to those skilled therein as of the date of the invention described and claimed herein.

The invention described in this application concerns the production of an *Eimeria tenella* sporozoite protein by recombinant DNA methods for use as a vaccine against coccidiosis in chickens.

It has been estimated that $0.5–$1.0 billion is spent annually by poultry producers worldwide in an effort to curb the devastating effect of coccidiosis in chickens (21,31). Even with control measures currently in use, poultry losses are substantial with estimates in the multimillion dollar range (36).

Eimeria are protozoan parasites whose entire life cycle is completed within a single host. The complex life cycle consists of both asexual and sexual stages. Chickens initially become infected upon ingestion of sporulated oocysts in contaminated feces, food or water. The sporulated oocysts except within the digestive tract as a result of the combined action of mechanical shearing and enzymatic hydrolysis of the sporocyst cap. The liberated sporozoites penetrate intestinal epithelial cells and undergo development which proceeds to the level of first generation meronts. Development of first generation merozoites follows due to muliple fission of meronts. The release of merozoites destroys the host cell and the parasites invade new host cells to produce a second and third asexual cycle. The pathology of coccidiosis due to *E. tenella* and some other species is related largely to the rupture of host cells during the release of merozoites. Bleeding in the gut is related to rupture of small capillaries servicing the epithelium. Sexual development commences with the production of microgametes and macrogametes through the process of gametogenesis. Liberated microgametes fertilize macrogametes to form zygotes. Following rupture of the host cell, immature oocysts are released and passed through the feces to the environment where they mature (sporulate) and become infective to chickens. Death generally occurs within 4–7 days in infected birds.

Currently, the most widely used means of controlling Eimeria in chickens is through the application of antiprotozoal chemical feed additives. The specific composition varies with the coccidiostat used, and each product affects only certain stages of the coccidian life cycle (21,30,33). There are many disadvantages to using coccidiostats, including short-duration protection in birds, occasional diminished performance, development of resistance to the drug in parasites and potentially, safety to workers and consumers. Use of coccidiostats requires the maintenance of at least two feed supplies since the majority of the drugs must be withdrawn before birds are marketed or before use for egg production. During the period of drug withdrawal birds are susceptible to coccidiosis. Products may remain on the market for only a few years because of the development of drug resistant strains. This adds considerable pressure on the cost of development and continued manufacture of efficacious products (30).

Protection of birds by immunization has met with some success. Investigators have been able to invoke limited protection using preparations of killed organisms (1,23,24). A more effective approach for immunization of chickens has been with the use of a live vaccine product—e.g., Coccivac TM (8). The product, being a multivalent composition containing low doses of viable oocysts, is administered in drinking water to invoke a mild parasitemia in birds. A drawback of this product has been occasional depressed performance of birds during the first weeks following administration. Variables such as excessive dosing or moisture content of bedding have even led to severe outbreaks of coccidiosis. See also, U.S. Pat. No. 3,147,186 which concerns the use of viable, sporulated oocysts of *E. tenella* to immunize chickens and U.S. Pat. No. 4,301,148 which concerns the use of sporozoites of *E. tenella* for the same purpose.

An alternative means of introducing the live vaccine into broiler houses is by way of the feed. This has been considered in a recent British patent (GB No. 2,008,404A). Prior to mixing with the feed, fully virulent ooctysts of *E. tenella* are encapsulated in a water soluble polysaccharide to protect against desiccation. The oocysts are in sufficient amounts only to induce subclinical infection. Though the immunizing ability was found to be excellent, no development of this method is foreseen due to questionable field acceptability. However, if attenuated strains of all the important coccidia could be developed, the procedure may be more acceptable.

Efforts have been made to develop Eimeria lines of reduced virulence. Some species have been successfully attenuated through chicken embryo passage (10,19,22,39). These strains have diminished ability to cause disease, yet have retained sufficient immunogenicity to invoke immunity. Some problems do, however, remain with the handling of these strains. As examples, the attenuated variants of *E. necatrix* have a critical passage limit whereby more or less embryo passage can result in loss of immumogenicity or maintenance of the original virulent force. Furthermore, some attenuated organisms revert to the virulent form upon minimal back-passage through chickens (20,41). Thus, problems associated with maintaining consistent properties in attenuated organisms are apparent.

Attenuation by precocious selection has also been practiced when Eimeria strains cannot be readily passaged through embryonated eggs. In this process, shed oocysts are harvested late in the prepatent period prior to the onset of heavy oocyst shedding (13,28,29,40). Such selection results in cultures having abbreviated life cycles, and a corresponding diminution in virulence properties (13,28,29,40). Though the trait of precocity for *E. tenella* (14) and *E. acervulina* (27) has been demonstrated to be genetically stable, not enough information is known about this method to assess its usefulness as a tool in the poultry industry.

Due to the large economic losses caused by coccidiosis in chickens, a vaccine against *E. tenella* and *E. necatrix* is desirable. Using hybridoma technology we have identified and purified potential protective antigens for use in subunit vaccines. Use of such a subunit vaccine avoids vaccine strain-related outbreaks and reversions or changes in immunological properties associated with the use of a live vaccine.

Subunit approaches to vaccine development have proven successful over the past few years. In such approaches, candidate protective antigens have been identified and characterized for the purpose of eventual preparation on a large scale. In studying parasite antigens, one research group used monoclonal antibodies to identify a potential protective antigen on the surface of *Babesia bovis* (53). A *B. bovis* antigen of 44,000 daltons has been identified, which when purified and injected into experimental animals afforded some level of protection against primary challenge. An immunologically important 30,000 dalton protein of *Toxoplasma sondii* has also been identified using monoclonal antibodies (16).

Since mid-1981, Danforth and coworkers have published several papers in which they indicate the possibility of producing monoclonal antibodies toward antigens of avian Eimeria speces (5,6,7). Similarly, Speer et al., (42,43) have demonstrated the development of hybridomas against *E. tenella* and some physiological properties thereof. Antibody-secreting hybridomas were selected on the basis of an indirect fluorescent antibody test (6). The patterns of reaction, as observed with ultraviolet microscopy, varied depending upon the monoclonal antibody used. Patterns have included exclusive reaction with sporozoites only vs. reaction with sporozoites and merozoites; staining of the anterior portion of the sporozoite vs. the entire membrane; and staining of distinct internal organelles vs. non-descript internal staining (7).

There is little information available about the surface antigens of avian coccidia. Previous work (51) identified approximately sixteen polypeptides ranging in molecular weight from 20,000 to greater than 200,000 daltons by surface iodination of excysated sporozoites.

Hybridoma cell lines which secrete monoclonal antibodies directed to antigens on the surface of sporozoites of *Eimeria tenella* have been reported (52). The antigens were not identified, other than that their molecular weights were between 13 and 150 kilodaltons. More recently monoclonal antibodies and their protein targets were generally described in European patent publication No. 0 135 712, published Apr. 3, 1985. In addition, the use of detergent solubilized, non-fractionated, sporozoite membrane extracts as a vaccine was described. Antigens and monoclonal antibodies reactive against merozoites of *E. tenella* were described in European patent publication No. 0 135 073, published Mar. 27, 1985.

A monoclonal antibody, Ptn 7.2 A4/4 produced by hybridoma cell line ATCC No. HB 8561 which neutralized *E. tenella* and *E. necatrix* sporozoites in vitro and conferred passive protection against coccidiosis due to *E. tenella* and *E. necatrix* in chickens has been isolated. Further experiments using immunoblotting and immunoprecipitation procedures identified the sporozoite protein target of this neutralizing monoclonal antibody. This protein is referred to as the TA4 antigen. The purified TA4 antigen is capable of inducing an immune response in a chicken that confers protection against infection by *E. tenella* and *E. necatrix.*

The quantity of parasite antigens that can be prepared from the organism is quite low and very costly. Recombinant DNA cloning and expression techniques have opened up a new approach to producing large amounts of protective antigens inexpensively. In simplest terms, these techniques require that DNA sequences encoding all or part of the antigen be placed in a cell, under the control of the genetic information necessary to produce the antigenic protein in that cell. The genetic information may be synthetic DNA (9), genomic (e.g., viral) or chromosomal DNA, or cDNA made from the mRNA encoding the antigen. The latter approach is the most direct method for complex organisms such as Eimeria sp.

However, because the cDNA only contains genetic information corresponding to the amino acid sequence of the antigen, it must be inserted into expression vectors that provide the genetic signals necessary for expression of the cDNA gene (i.e., transcription and translation). The antigens can be synthesized either alone or as products fused to another protein *E. coli.*

Production of an effective subunit vaccine in *E. coli* has been reported for foot and mouth disease virus of swine and cattle (17,38). Foot and mouth disease virus surface antigens were produced as fusion protein antigens in *E. coli.* Significant levels of virus-neutralizing antibody were raised when cattle and swine were immunized with these antigens. The recombinant DNA-derived antigens gave protection against challenge with foot and mouth disease virus.

In contrast to simple organisms such as foot and mouth disease virus where the genome and surface proteins have been studied extensively, very little is known about the molecular biology of *Eimeria tenella.* In addition, Eimeria has a complex life cycle. Wang and Stotish (49,50) reported rapid but transient RNA and protein synthesis during the first 6–8 hours after initiation of sporulation and suggested that all protein and nucleic acid synthesis during sporulation occurs in these first few hours. For example, Stotish et al. (44) reported a 30,000 dalton glycoprotein protein component of sporozoite membranes that was synthesized by unsporulated oocysts and later incorporated into sporozoite membranes during the process of sporulation. Recently, Stotish et al. (45) reported isolation and in vitro translation of RNA from unsporulated oocysts, oocysts during sporulation and from sporozites. The in vitro translation products ranged from less than 10,000 daltons to greater than 200,000 daltons. Patterns for unsporulated and sporulating oocyst RNA directed-protein synthesis were different, suggesting that different RNA populations may exist during sporulation.

In order to produce the cDNA encoding the TA4 protein, it was necessary to determine when the TA4 mRNA occurred during the life cycle of *E. tenella.* This invention concerns the isolation and characterization of a cDNA clone encoding the TA4 protein as a continuous 25,000 dalton polypeptide and production of engineered TA4 antigenic proteins in *E. coli.* It also concerns the extraction of TA4 proteins produced in *E. coli* from the insoluble state and the process to make the proteins immunoreactive with monoclonal antibody Ptn 7.2 A4/4. Finally, this invention shows the preparation and use of the bacterially produced TA4 proteins to produce immunity in chickens to coccidiosis caused by *E. tenella*.

SUMMARY OF THE INVENTION

A genomic DNA molecule having the nucleic acid sequence set forth in FIG. 1 and encoding an antigenic protein derived from *Eimeria tenella* has been isolated. The native protein has a molecular weight of about 25,000 daltons and is composed of two polypeptides joined by a disulfide bond. One of the polypeptides is characterized by a molecular weight of about 17,000 daltons and by a blocked N-terminal amino acid and has the amino acid sequence set forth in FIG. 1. The other polypeptide is characterized by a molecular weight of about 8,000 daltons and has the amino acid sequence set forth in FIG. 1.

A nucleic acid molecule, which is either cDNA or mRNA, encoding an antigenic polypeptide having a molecular weight of about 25,000 daltons and having the continuous amino acid sequence set forth in FIG. 4 has also been isolated. The cDNA molecule has been inserted into expression vectors capable of expressing the 25,000 daltons polypeptide directly or as a fused polypeptide.

Vector pDET1 encodes a polypeptide having a molecular weight of about 25,000 daltons and the continuous amino acid sequence set forth in FIG. 4. This vector was used to transform *E. coli* host cells and the strain deposited as REN3/pDET1 (ATCC accession No. 53316).

Vector pDET2 also encodes a polypeptide having a molecular weight of about 25,000 daltons and the continuous amino acid sequence set forth in FIG. 4. This vector was used to transform *E. coli* host cells and the strain deposited as REN3/pDET2 (ATCC accession No. 53318).

Vector pBGC23 encodes a fused polypeptide having a molecular weight of about 135,000 daltons which has the amino acid sequence of the 25,000 dalton polypeptide set forth in FIG. 4 and, at the amino terminal end, the amino acid sequence of beta-galactosidase. This vector was used to transform *E. coli* host cells and the strain deposited as REN3/pBGC23 (ATCC accession No. 53317).

Vector pCOC12 encodes a fused polypeptide having a molecular weight of about 65,600 daltons and having the amino acid sequence of the 25,000 dalton polypeptide set forth in FIG. 4 and, at the amino terminal end, the amino acid sequence of prochymosin. This vector was used to transform *E. coli* host cells and the strain deposited as REN3/pCOC12 (ATCC accession No. 53314).

Vector pCOC20 encodes a fused polypeptide having a molecular weight of about 56,000 and having the amino acid sequence of the 25,000 dalton polypeptide set forth in FIG. 4 and, at the amino terminal end, the amino acid sequence of prochymosin which has an 83 amino acid deletion from its natural sequence. This vector was used to transform *E. coli* host cells and the strain deposited as REN3/pCOC20 (ATCC No. 53313).

A method of preparing an antigenic polypeptide, comprises growing any of the host cells of the present invention under appropriate conditions permitting DNA expression and polypeptide production and recovering the polypeptide so produced under suitable conditions. The recovery comprises separating the polypeptide from host cells, purifying the polypeptide, solubilizing the polypeptide, renaturing the polypeptide, and recovering the purified, solubilized, renatured antigenic polypeptide.

A method of conferring upon a chicken active immunity against infection by *Eimeria tenella* comprises administering to a chicken an effective immunizing amount of any of the polypeptides of the present invention.

BRIEF DESCRIPTION OF THE FIGURES

FIG. 1 shows the DNA nucleotide sequence of the Bgl II-EcoRI DNA fragment of the *E. tenella* genomic clone 108-1 encoding the TA4 protein. The amino acid sequence for the signal peptide and the 17,000 and 8,000 dalton polypeptide components of the TA4 antigen as it occurs in the sporozoite membrane is also shown. FIG. 1 also shows the introns within the gene as well as the SacI-PvuII DNA used to identify the mRNA by hybridization, and cDNA clones encoding the TA4 protein.

FIG. 4 shows the DNA sequence of the cDNA clone pTCD26 encoding the TA4 antigen.

FIG. 10 also shows the derivation of pCOC20 from pCOC12.

DETAILED DESCRIPTION OF THE INVENTION

Figure 2:
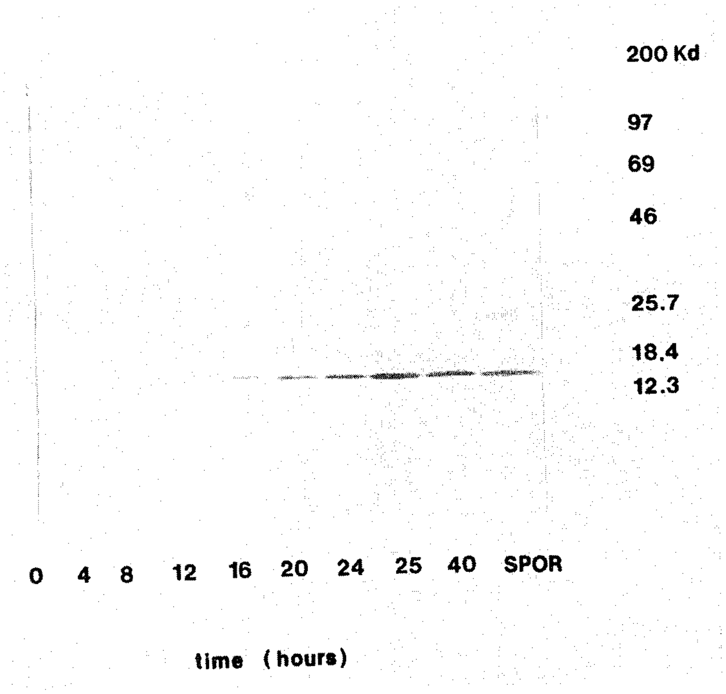
FIG. 2 shows the appearance of the TA4 antigen during sporulation as determined by the appearance of a 17,000 dalton subunit immunoreactive with monoclonal antibody Ptn 9.9 D12.

A genomic DNA molecule having the nucleic acid sequence set forth in FIG. 1 and encoding an antigenic protein derived from *Eimeria tenella* has been isolated. The native protein has a molecular weight of about 25,000 daltons and is composed of two polypeptides joined by a disulfide bond. One of the polypeptides is characterized by a molecular weight of about 17,000 daltons and by a blocked n-terminal amino acid and has the amino acid sequence set forth in FIG. 1. The other polypeptide is characterized by a molecular weight of about 8,000 daltons and has the amino acid sequence set forth in FIG. 1.

A nucleic acid molecule, which is either cDNA or mRNA, encoding an antigenic polypeptide having a molecular weight of about 25,000 daltons and having the continuous amino acid sequence set forth in FIG. 4 has also been isolated.

A DNA molecule encoding an antigenic polypeptide having a molecular weight less than about 25,000 daltons and an amino acid sequence included within the amino acid sequence of the protein encoded by the DNA having the nucleic acid sequence set forth in FIG. 1 is contemplated. This DNA molecule may also have additional DNA encoding another amino acid sequence, in which case the molecular weight of the polypeptide would be increased by the molecular weight of the additional amino acid sequence.

A DNA molecule encoding an antigenic polypeptide having a molecular weight greater than about 25,000 daltons which comprises the genomic DNA molecule of the present invention and DNA encoding another amino acid sequence is contemplated.

A DNA molecule encoding an antigenic polypeptide having a molecular weight less than about 25,000 daltons and an amino acid sequence included within the amino acid sequence of the polypeptide encoded by the DNA having the nucleic acid sequence set forth in FIG. 4 is contemplated. This DNA molecule may also have additional DNA encoding another amino acid sequence, in which case its molecular weight would be increased by the molecular weight of the additional amino acid sequence.

The present invention provides a DNA molecule encoding an antigenic polypeptide having a molecular weight greater than about 25,000 daltons which comprises the nucleic acid molecule set forth in FIG. 4 and DNA encoding another polypeptide amino acid sequence.

A recombinant cloning vehicle comprises cloning vehicle DNA and the cDNA of the present invention. The cloning vehicle DNA being characterized by the presence of a first and a second restriction enzyme site and the cDNA being cloned into said sites. A cloning vehicle has been constructed which contains the cDNA clone, designated pTCD26, of the present invention and encodes an antigenic polypeptide having a molecular weight of about 25,000 daltons and the amino acid sequence set forth in FIG. 4. The cloning vehicle may be used to transform a bacterial host cell. An *E. coli* host cell, JM83 has been transformed with this cloning vehicle and the strain designated as JM83/pTCD26 (ATCC accession No. 53315).

The present invention contemplates an expression vector capable of expressing a 25,000 dalton antigenic protein when introduced into a suitable host cell, which comprises suitable carrier DNA and the genomic DNA set forth in FIG. 1.

When referring to an expression vector carrying the genomic DNA of the present invention, a suitable host cell is a euraryotic cell, i.e. a yeast cell or mammalian cell. Otherwise, a suitable host cell is a bacterial host cell, i.e. *E. coli.*

Also contemplated is an expression vector capable of expressing an antigenic polypeptide having a molecular weight less than about 25,000 daltons, when introduced into a suitable host cell. The vector comprises suitable carrier DNA and DNA encoding an antigenic polypeptide having a molecular weight less than about 25,000 daltons and an amino acid sequence included within the amino acid sequence of the protein encoded by the DNA having the nucleic acid sequence set forth in FIG. 1 or FIG. 4. The non-carrier DNA may also have additional DNA encoding another amino acid sequence, in which case the molecular weight of the polypeptide would be increased by the molecular weight of the additional amino acid sequence.

Suitable carrier DNA would be any DNA segment capable of carrying the genomic DNA molecule of the present invention for use in transforming eucaryotic cells. One such suitable carrier DNA would be that derived from a eucaryotic virus, preferably a commonly used avian virus, such as Marek's disease virus, fowl pox virus or herpes virus of turkeys (HVT) or any mutant derivative thereof.

Also contemplated is an expression vector capable of expressing an antigenic polypeptide having a molecular weight greater than 25,000 daltons, when introduced into a suitable host cell, which comprises suitable carrier DNA and the genomic DNA molecule of the present invention and DNA encoding another amino acid sequence.

A bacterial expression vector capable of expressing a 25,000 dalton antigenic polypeptide when introduced into a suitable bacterial host cell, comprises plasmid DNA and the cDNA of the present invention. When under the control of the lac, lambda $P_R$ and tac promoters this vector is designated pDET1. When under the control of the lac and tac promoters this vector is designated pDET2.

A suitable bacterial expression vector is a double-stranded DNA molecule which includes in 5' to 3' order the following:

- a DNA sequence which contains a promoter and operator or just a promoter;
- a DNA sequence which contains a ribosomal binding site for rendering the mRNA of the desired gene capable of binding to ribosomes within the host cell
- an ATG initiation codon;
- a restriction enzyme site for inserting a desired gene into the vector in phase with the ATG initiation codon;
- a DNA sequence which contains an origin of replication from a bacterial plasmid capable of autonomous replication in the host cell; and
- a DNA sequence which contains a gene associated with a selectable or identifiable phenotypic trait and which is manifested when the vector is present in the host cell.

The present invention contemplates a bacterial expression vector capable of expressing an antigenic polypeptide having a molecular weight less than about 25,000 daltons when introduced into a suitable bacterial host cell. The vector comprises plasmid DNA and DNA which encodes a polypeptide having an amino acid sequence included within the amino acid sequence set forth in FIG. 4. The non-plasmid DNA may also have additional DNA encoding another amino acid sequence, in which case the molecular weight of the polypeptide would be increased by the molecular weight of the additional amino acid sequence.

The present invention provides a bacterial expression vector capable of expressing a fused polypeptide composed a polypeptide of about 25,000 daltons fused to another amino acid sequence when introduced into a suitable host cell. It comprises plasmid DNA and the cDNA of the present invention fused to DNA encoding another amino acid sequence.

The vector pBGC23 encodes an antigenic fused polypeptide having a molecular weight of about 135,000 daltons and having the amino acid sequence of beta-galactosidase fused to the amino terminal end of the amino acid sequence set forth in FIG. 4.

The vector PCOC12 encodes an antigenic fused polypeptide having a molecular weight of about 65,600 daltons and having the amino acid sequence of prochymosin fused to the amino terminal end of the amino acid sequence set forth in FIG. 4.

The vector pCOC20 encodes an antigenic fused polypeptide having a molecular weight of about 56,500 daltons and having the amino acid sequence of prochymosin, which has an 83 amino acid deletion from its natural sequence, fused to the amino terminal sequence set forth in FIG. 4.

The bacterial expression vectors of the present invention have been used to transform *E. coli* host cells. The *E. coli* host cell designated REN3/pBGC23 comprises the vector pBGC23 and has ATCC accession No. 53317. The *E. coli* host cell designated REN3/pCOC12 comprises the vector pCOC12 and has ATCC accession No. 53314. The *E. coli* host cell designated REN3/-pCOC20 comprises the vector pCOC20 and has ATCC accession No. 53313. The *E. coli* host cell designated REN3/pDET1 comprises the vector pDET1 and has ATCC accession No. 53316. The *E. coli* host cell designated REN3/pDET2 comprises the vector pDET2 and has ATCC accession No. 53318.

A method of preparing an antigenic polypeptide, comprises growing any of the host cells of the present invention under appropriate conditions permitting DNA expression and polypeptide production and recovering the polypeptide so produced under suitable conditions. The recovery step comprises first separating the polypeptide from host cells and then purifying it, solubilizing it, renaturing it and finally recovering the purified, solubilized, renatured antigenic polypeptide.

A method of conferring upon a chicken active immunity against infection by *Eimeria tenella* comprises administering to a chicken an effective immunizing amount of any of the polypeptides of the present invention. The polypeptides may also be administered in any combination of two or more polypeptides.

A vaccine for conferring upon a chicken active immunity against infection by *Eimeria tenella* comprises per dose an effective immunizing amount of any one of the polypeptides of the present invention and a suitable carrier. The vaccine may also comprise a combination of two or more polypeptides of the present invention and a suitable carrier. In one embodiment, the polypeptide used in the vaccine is the fused polypeptide having a molecular weight of about 135,000 daltons and the amino acid sequence of beta-galactosidase fused to the amino terminal end of the amino acid set forth in FIG. 4. In another embodiment the polypeptide used in the vaccine is the fused polypeptide having a molecular weight of about 65,600 daltons and having the amino acid sequence of prochymosin fused to the amino terminal end of the amino acid sequence set forth in FIG. 4.

A method of protecting a chicken against infection by *Eimeria tenella* comprises administering to the chicken a suitable dose of any of the vaccines of the present invention.

Plasmid pDET1 encodes a 25,000 dalton polypeptide under the control of the lac, lambda $P_R$ and tac promoters.

Figure 5:
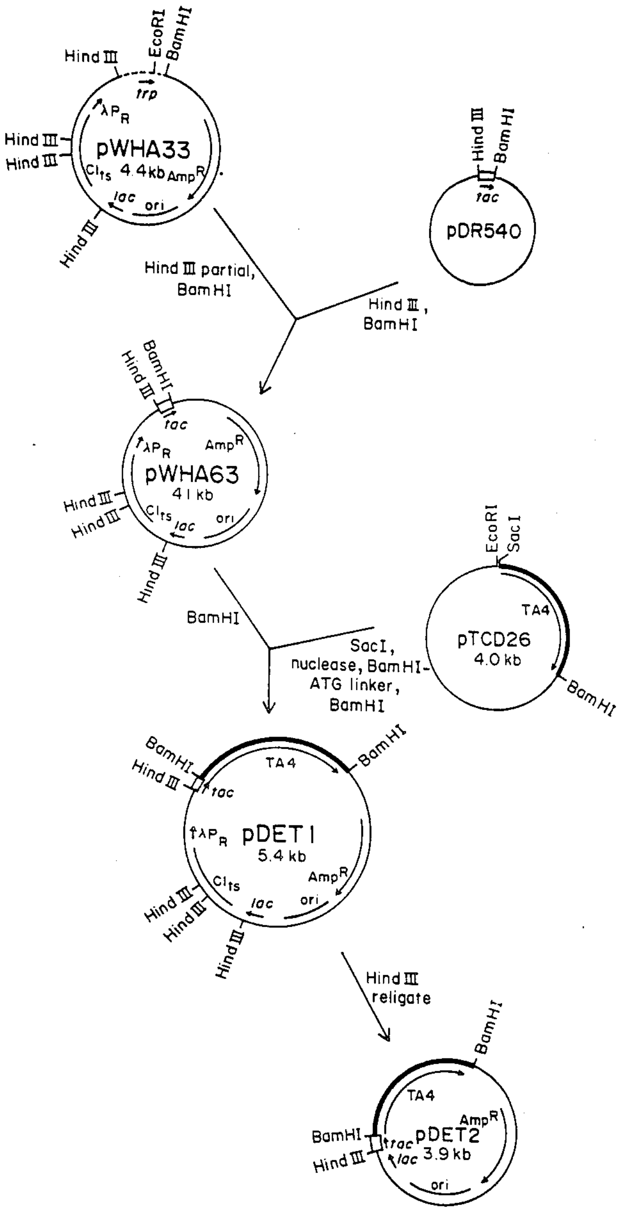
FIG. 5 schematically shows the construction of expression vector pWHA63 and the insertion of the DNA from the cDNA clone pTCD26 into expression vector pWHA63 to generate expression vectors pDET1 and pDET2.
Figure 6:
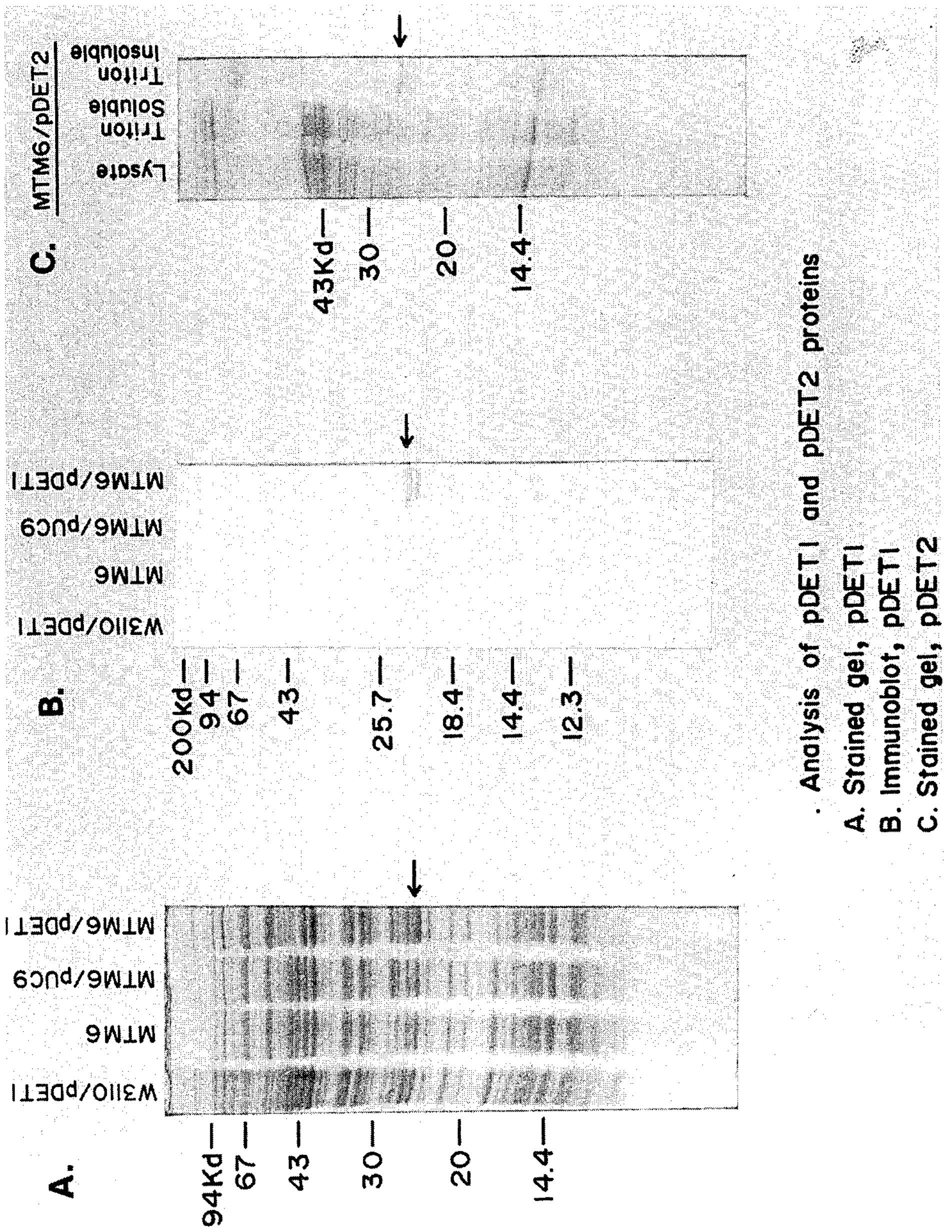
FIG. 6 shows the production of the pDET1/pDET2 protein in Lon+ vs. Lon− protease deficient strains of *E. coli*.

Plasmid pDET2 encodes a 25,000 dalton polypeptide under the control of the lac and tac promoters (FIG. 5). The greatest yield of the pDET1/pDET2 proteins was achieved in a protease deficient *E. coli* strain (FIG. 6). The pDET1 and pDET2 proteins were found in the insoluble fraction of a cell lysate.

Figure 7:
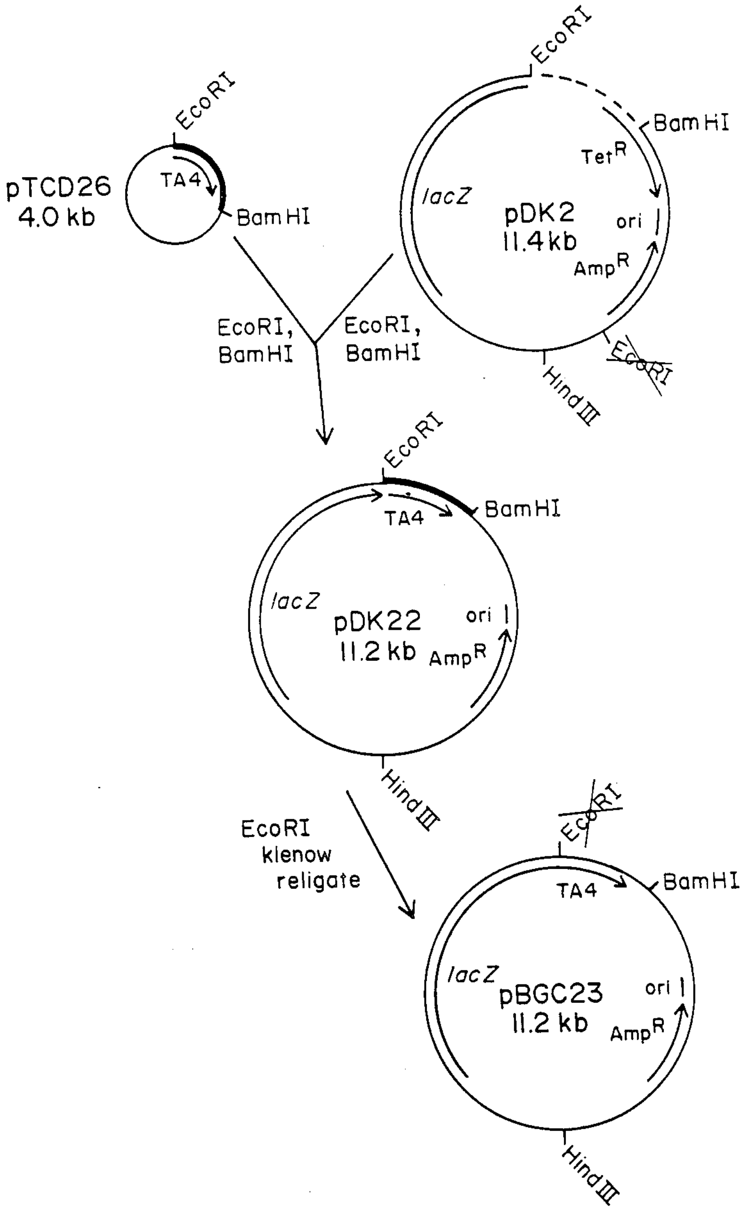
FIG. 7 schematically shows the construction of expression vector pBGC23 fusing the 3′ end of the lac Z gene to the 5′ end of the sequence encoding the cDNA derived antigenic polypeptide.
Figure 8:
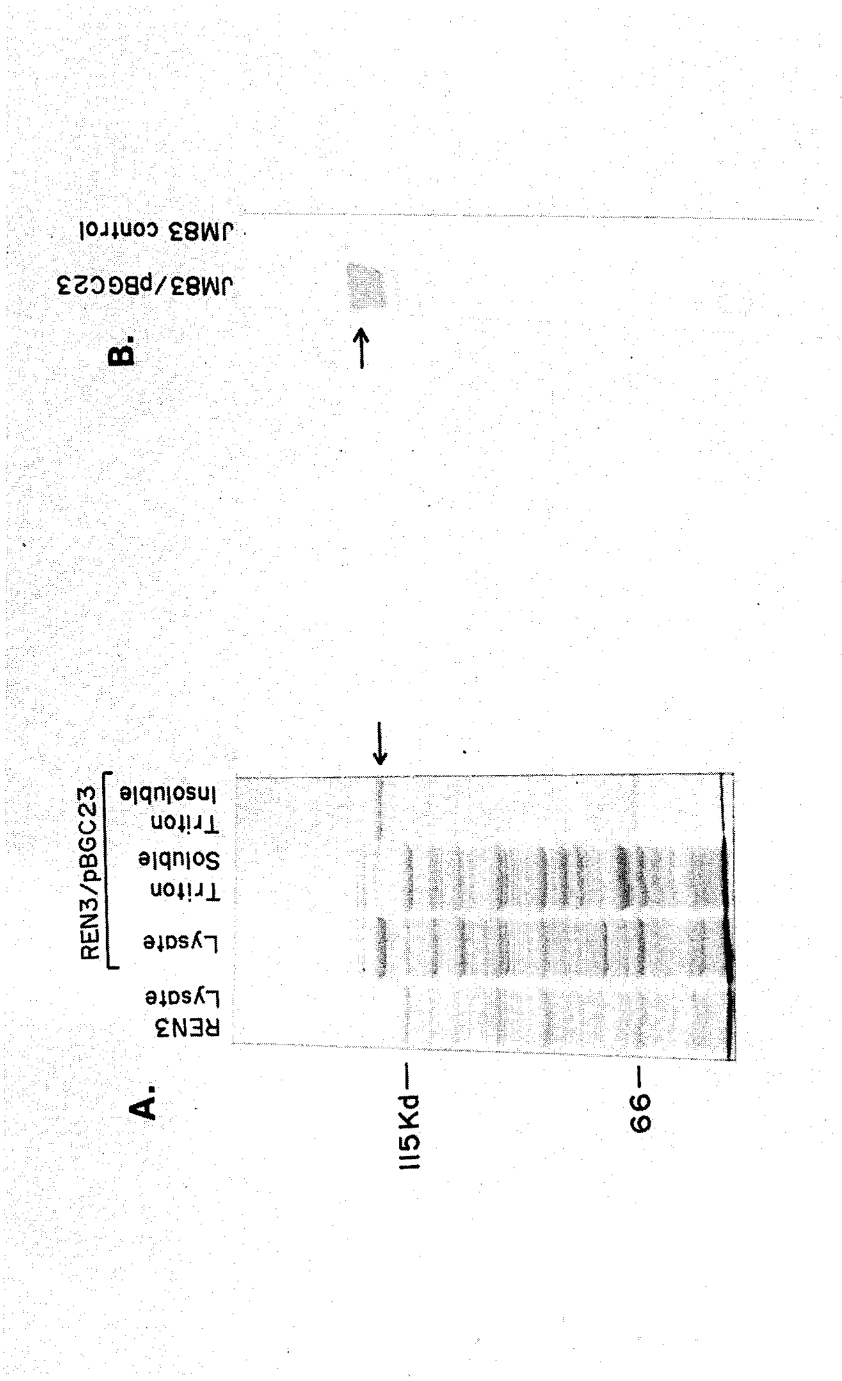
FIG. 8 shows the production of the pBGC23 protein in *E. coli*.

Plasmid pBGC23 was constructed by fusing the 3′ end of the coding sequence of *E. coli* beta-galactosidase to the 5′ end of the coding sequence of the cDNA derived TA4 polypeptide and encodes a fusion protein of approximately 135,000 daltons (FIG. 7). The pBGC23 protein is stable but insoluble in *E. coli* (FIG. 8).

Figure 10:
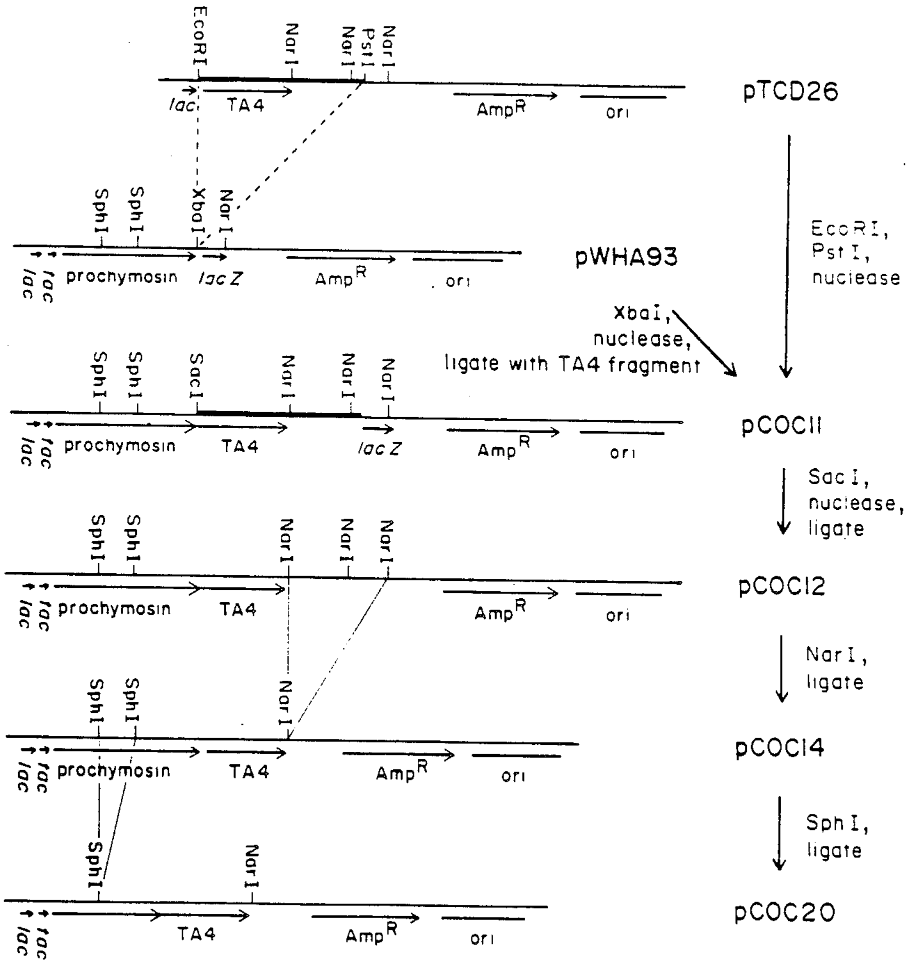
FIG. 10 schematically shows the construction of pCOC12 by fusing the 3′ end of the coding sequence of bovine prochymosin to the 5′ end of the coding sequence of the cDNA derived antigenic polypeptide.
Figure 11:
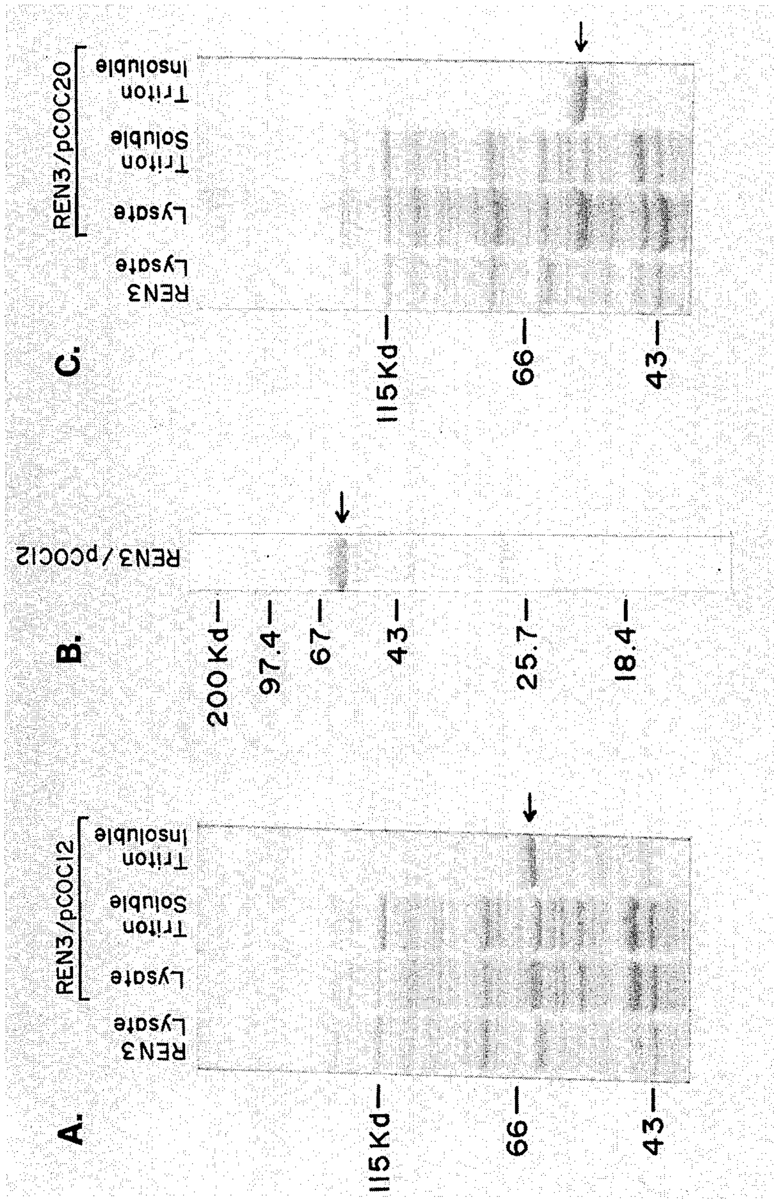
FIG. 11 shows the production of the pCOC12 and pCOC20 proteins in *E. coli*.

Plasmid pCOC12 was constructed by fusing the 3′ end of the coding sequence of bovine prochymosin to the 5′ end of the cDNA derived TA4 polypeptide and encodes a fusion protein of approximately 65,600 daltons. Plasmid pCOC20 was constructed from pCOC12 by a deletion in the prochymosin domain of the fusion protein and encodes a fusion protein of approximately 56,500 daltons (FIG. 10). The pCOC12 and pCOC20 proteins are stable but insoluble in *E. coli* (FIG. 11).

The insoluble, bacterially-produced TA4 proteins were not immunoreactive with Ptn 7.2 A4/4, a neutralizing monoclonal raised to *E. tenella* sporozoites. When the insoluble proteins from pBGC23 and pCOC12 were injected into mice they did not raise antibodies that cross-reacted with the TA4 antigen purified from *E. tenella.*

This invention also concerns a method for extracting the bacterially-produced TA4 proteins from the insoluble state and the process to make the proteins immunoreactive with monoclonal antibody Ptn 7.2 A4/4. This method is applicable to renaturation of prochymosin-TA4 fusion proteins to make them immunoreactive. It involves solubilization of the proteins in 8M urea followed by dilution and renaturation at alkaline pH (pH 11) and back titration to pH 8.3. Alternatively the proteins may be solubilized in 8M urea and the urea removed by dialysis.

When the urea-alkali solubilization/renaturation process was used for the pCOC12 protein the renatured protein had both milk clotting activity and immunoreactivity with monoclonal antibody Ptn 7.2 A4/4. Renaturation conditions were optimized using the pCOC12 protein. The optimal renaturation conditions for pCOC20 protein and pBGC23 protein were found to be the same as those for pCOC12. For pDET2 protein on the other hand optimal renaturation conditions involved urea-dialysis at alkaline pH.

The renatured pBGC23 and pCOC12 proteins elicited antibodies in mice that reacted with the TA4 antigen purified from *E. tenella.* When chickens were immunized with renatured pBGC23 and pCOC12 proteins these proteins elicited serum neutralizing antibodies to *E. tenella* sporozoites and ameliorated coccidiosis in chickens challenged with *E. tenella.*

This invention also encompasses a method for conferring upon a chicken active immunity against infection by *Eimeria tenella* which comprises administering to a chicken an effective immunizing amount of the renatured bacterial TA4 proteins. By this method active immunity can be conferred upon a non-immune chicken. In addition, administration of these materials can be used to increase a relatively low level of immunity in a chicken previously exposed to *E. tenella* and can be used in booster vaccinations.

The bacterial TA4 proteins can be administered to chickens by any of a number of well known methods. Desirably, the administration can involve subcutaneous or intramuscular injection at the back of the neck, or any convenient form of oral administration. The amount of anitgen comprising an effective immunizing amount can be any amount from about 0.1 microgram to about 1 mg. The amount of antigen is desirably above about 10 micrograms. The preferred amount of antigen is about 500 micrograms per kilogram of body weight. Alternatively, the administration can be oral (e.g., via capsule) or desirably by injection (e.g., subcutaneous, intradermal, or preferably intramuscular injections). If the mode of administration involves injection, any pharmaceutically acceptable carrier can be employed. Suitable carriers include 0.01 to 0.1M, preferably 0.05M, phosphate buffer or 0.8 percent saline.

A vaccine for conferring upon a chicken active immunity against infection by *Eimeria tenella* is provided which comprises an effective immunizing amount of an antigenic material of this invention, i.e., the renatured bacterial TA4 proteins and a suitable carrier. Preferably the effective immunizing amount of the antigenic material in the vaccine is above about 0.1 microgram/kg of body weight of the chicken.

In addition, the carrier desirably also contains a preservative. One particularly suitable preservative is thimerosal (sodium ethylmercurithiosalicylate) which has activity as both a bacteriostat and a fungistat. Desirably, thimerosal is present in the vaccine in a final concentration of $10^{-4}$ percent.

Furthermore, the carrier desirably also contains an immunopotentiator. Various immunopotentiators known in the art may be used. The adjuvant presently employed is 94% Drakeol 6-VR, 5% Arlacel A, 1% Tween-80. Arlacel A is a mannide monoleate (Sandria Corp.). It is an irritant which has strong immunopotentiating activity when combined with antigens. Drakeol 6-VR is a hypoallergenic light mineral oil product (Penreco Corp.). Tween-80 is a monoleate derivative of polyoxyethylsorbitan and possesses detergent properties. Other suitable carriers or immunopotentiators include aluminum potassium sulfate, aluminum hydroxide, ligand binding subunits of toxin molecules, bioadhesives, lymphokines and water in oil emulsions.

By administering a suitable dose of such a vaccine to a chicken, the chicken is protected against infection by *E. tenella*. The amount of antigenic material per dose should be sufficient to induce production of antibodies to the antigenic material in an animal to which the vaccine is administered. To provide a sufficient degree of immunological response as measured by antibody production and protection, the amount of the antigenic material per dose is desirably above about 20.0 micrograms/kg of body weight of the vaccinated animal. Thus, the amount of antigenic material based upon a 50 gram day-old chick would be above about 1.0 microgram. Presently preferred is a vaccine containing 10 micrograms of antigenic material. In general, the antigen will comprise on a weight basis from about 0.002 percent up to about 0.2 percent of the vaccine and the dose volume will be about 0.1 ml.

EXAMPLE 1

Preparation of *Eimeria tenella* Oocysts, Sporocysts and Sporozoites

Coccidia

The purified field isolate of *Eimeria tenella* used for these experiments was originally purchased from Dr. Allen Edgar of the University of Auburn. The purity of this *E. tenella* isolate was confirmed using oocyst characteristics and histology of infected intestinal tissue. Oocyst size and shape index were within the range of *E. tenella.*

Lesions were scored by the method of Johnson and Reid (15). The lesions in infected birds were typical for *E. tenella.* The pathology was limited to the ceca and consisted of severe hemorrhage and tissue damage. At 5 days post-infection histological examination revealed larger second generation schizonts in the subepithelium of the ceca. Mortality was common with severe infections (15,000 oocysts). Single oocyst cloning was periodically done to insure purity of the *E. tenella* isolate.

Propagation of Oocysts

Pure cultures of this isolate were routinely passaged in 4- to 6-week old SPF white leghorn chickens. To avoid extraneous coccidial infections, chickens were reared from 1 day of age in plexiglass isolation units. Oocysts were harvested on day 7 post-infection from the ceca using a trypsin-digest method described by Shirley (39). Sporulated oocysts were typically stored at 24° C. in 2% w/v $K_2Cr_2O_7$.

Isolation of Sporocysts

Sporulated *Eimeria tenella* oocysts, ($1\times10^8$) which had been partially purified from debris by salt flotation, were washed five times in 0.1M phosphate buffered saline, pH 7.4, (PBS) to remove the potassium dichromate preservative. These oocysts were further cleaned by agitation in a 1.05% sodium hypochlorite solution for 15 minutes followed by five washes in PBS to remove residual sodium hypochlorite and debris. Following the final wash, the cleaned oocysts were resuspended in 10 ml of PBS. Suspended oocysts were then mechanically broken by shaking with an equal volume of glass beads (1.0–1.05 mm). The liberated sporocysts were purified from the oocyst walls and from unbroken oocysts by passage over a glass wool column, centrifuged at 10,000 RPM for ten minutes at 4° C. and resuspended in 10 ml of PBS.

Preparation of Sporozoites

To excyst sporozoites, sporocysts were incubated with trypsin and taurodeoxycholic acid (0.25 and 0.50% w/v, respectively), for a period of 1 hour at 41° C. Sporozoites thus obtained were rinsed free of excysting fluid by centrifugation and resuspended in Hank's medium. Fresh Hank's medium was used to dilute sporozoites to the working concentration.

Preparation of Unsporulated Oocysts for Sporulation Time Course Studies

Oocysts were propagated and harvested as described in the preceding paragraph with the following modifications: all harvesting and preparations were done at 4° C. and all solutions contained 0.1 mM sodium dithionite to prevent the onset of sporulation (48). Oocysts were stored at 4° C. in 0.1 mM sodium dithionite for less than one week before sporulation was initiated. For sporulation time course studies 2–4×$10^9$ unsporulated oocysts were washed 3–4 times with cold deionized water to remove the dithionite. The suspension was centrifuged at 7–800×g for 10 minutes at 4° C. Oocysts were diluted with approximately 10 volumes of 1.05% sodium hypochlorite and shaken vigorously at room temperature. The residual sodium hypochlorite and debris was removed by 3 washes with cold sterile PBS. Oocysts were resuspended at a concentration of 2×$10^7$ oocysts/ml sterile PBS and sporulated by shaking gently at 30° C. for 36 to 48 hours. Aliquots were asceptically removed at various time points during sporulation as specified in the following examples.

EXAMPLE 2

Appearance of the TA4 Antigen During Sporulation

The TA4 antigen has been previously isolated and purified from *E. tenella* sporocyst membranes. It consists of two polypeptides, a 17,000 and an 8,000 dalton peptide which are bound to one another by a disulfide linkage.

A chromosomal DNA clone encoding the TA4 region has been isolated and th DNA sequence (FIG. 1) has shown the two peptides of the TA4 antigen are encoded by a contiguous nucleotide sequence. Hence, the 17,000 and 8,000 dalton peptides are derived from proteolytic processing of a single 25,000 dalton peptide. In addition, the DNA sequence encodes a "signal" sequence typically found transiently at the amino terminus of many secretory or membrane proteins.

In order to determine when in the process of sporulation the TA4 antigen occurs, its appearance was measured by immunoreaction with a specific monoclonal antibody, Ptn 9.9 D12. Monoclonal antibody Ptn 9.9 D12 is a sporozoite-neutralizing monoclonal antibody that reacts with the TA4 antigen. Reducing conditions destroy the reactivity of the TA4 antigen with monoclonal antibody Ptn 7.2 A4/4. However, on Western blots of SDS PAGE under reducing conditions monoclonal antibody Ptn 9.9 D12 reacts with the 17,000 dalton polypeptide component of the TA4 antigen.

Starting immediately after the final PBS wash (see Example 1) aliquots containing 1×$10^7$oocysts were removed for analysis at four hour intervals up to 24 hours and at 36 to 48 hours after sporulation was begun. Sporulating oocysts were centrifuged at 7–800×g for 10 minutes and the supernatant was removed. The pellets were quick-frozen in a dry ice/methanol bath and then stored at −70° C. until analysis.

Each pellet was thawed in 200 microliters of 20 mM Tris-HCl pH 7.5, 50 mM $MgCl_2$, 25 mM NaCl and an equal volume of glass beads. After shaking vigorously for 10 minutes 200 microliters of 2×SDS PAGE sample buffer (18) was added. Samples were boiled for 3 minutes, centrifuged to remove debris and 25–50 microliters of each sample was applied to SDS polyacrylamide gels (5–25% gradient) for analysis. Proteins were transferred to nitrocellulose sheets (3, 46). The remaining protein binding sites on the nitrocellulose were blocked with 3% (w/v) gelatin, 10 mM Tris-HCl pH 7.5, 150 mM NaCl, 0.05% (w/v) $NaN_3$ for 30 minutes at room temperature. Nitrocellulose filters were incubated with monoclonal antibody Ptn 9.9 D12 (approximately 10 micrograms/ml in 3% (w/v) bovine serum albumin, 10 mM Tris-HCl pH 7.5, 150 mM NaCl, 0.05% (w/v) $NaN_3$) overnight at 4° C. After washing the nitrocellulose filters three times with 50–100 ml of the antibody dilution buffer, the location and amount of bound monoclonal antibody Ptn 9.9 D12 was determined using the Vectastain TM ABC Kit for mouse IgG (Vector Laboratories, Inc., Burlingame, CA). Nitrocelulose filters were immersed in 20 ml of biotinylated horse anti-mouse IgG (80 microliters biotinylated anti-mouse antibody, 80 microliters normal horse serum in 20 ml antibody dilution buffer) and gently shaken for 30 minutes at room temperature. Nitrocellulose filters were rinsed three times with 50–100 ml of antibody dilution buffer without $NaN_3$. Nitrocellulose filters were then incubated with 15 ml of Vectastain TM ABC Reagent for 30 minutes at room temperature (80 microliters Avidin DH Reagent A mixed with 80 microliters biotinylated horseradish peroxidase Reagent B in 15 ml antibody dilution buffer without $NaN_3$ preincubated for 30 minutes before addition to the filters). After three washes bound horseradish peroxidase was measured by color development with 4-chloro-1-napthol (Sigma Chemical Co., St. Louis, MO). Blots were incubated with the color development solution (2 ml of 3 mg 4-chloro-1-napthol/ml methanol, 5 microliters 30% hydrogen peroxide in 10 ml 10 mM Tris-HCl pH 7.5, 150 mM NaCl) for 10–30 minutes. After appearance of the purple bands indicating the location and amount of Ptn 9.9 D12 reactive material, the nitrocellulose sheets were washed twice with water, air dried and stored in the dark.

The 17,000 dalton polypeptide component of the TA4 antigen that was immunoreactive with monoclonal antibody Ptn 9.9 D12 appeared between 16 to 24 hours after the initiation of sporulation and thereafter (FIG. 2). Sixteen hours corresponds with the beginning of elongation of the four structures destined to become sporocysts inside the sporulating oocyst.

EXAMPLE 3

Isolation and Identification of mRNA Encoding the TA4 Antigen

Before cDNA, could be synthesized it was necessary to determine when the mRNA encoding the TA4 antigen appeared during sporulation. Aliquots containing 2.5–5×$10^8$ oocysts were asceptically removed at four hour intervals up to 24 hours (including time 0) and at 36 to 48 hours after sporulation was begun. The sporulation oocysts were centrifuged at 7–800×g for 10 minutes and the supernatant was removed. The pellets were quick-frozen in a dry ice/methanol bath and then stored at −70° C. until RNA was isolated.

Each pellet was thawed in approximately 10 volumes of 5M guanidine thiocyanate, 20 mM Tris-HCl pH 7.5, 10 mM EDTA, 5% (v/v) beta-mercaptoethanol and oocysts were rapidly broken by shaking vigorously with an equal volume of 1.0 mm glass beads for 10 minutes. After bringing the samples to 2% (w/v) N-lauroylsarcosine they were centrifuged at approximately 8,000×g at room temperature to remove debris. RNA was isolated from the supernatant by sedimentation through a CsCl cushion (47).

The RNA pellet was resuspended in 20 mM Tris-HCl pH 7.5, 50 mM EDTA pH 8.0, 0.2% SDS, 100 units/ml RNasin TM (Promega Biotec, Madison, WI), 10 mM beta-mercaptoethanol. After extracting twice alternately with phenolchloroform:isoamyl alcohol (24:1) and chloroform:isoamyl alcohol (24:1) the RNA was precipitated and stored in ethanol at −20° C. Approximately 100–300 micrograms of total RNA was isolated from 2.5–5.5×$10^8$ oocysts.

PolyA-containing RNA was isolated by oligo-dT cellulose chromatography (2). Total RNA was loaded on an oligo-dT cellulose column (Type 3, Collaborative Research, Inc., Lexington, MA) in 10 mM Tris-HCl pH 7.5, 1 mM EDTA, 0.2% (w/v) SDS, 0.4M LiCl. RNA was eluted at 40° C. in the same buffer without LiCl. Approximately 5–15 micrograms A+ RNA was isolated from 2.5–5.0×$10^8$ oocysts.

Figure 3:
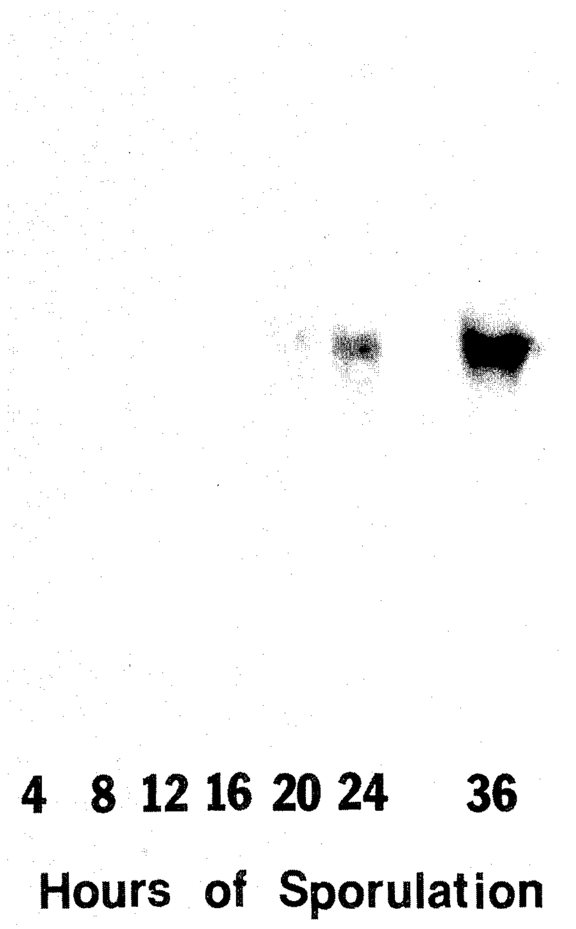
FIG. 3 shows the occurrence of the TA4 antigen mRNA during sporulation, as determined by hybridization of an internal restriction fragment from a genomic clone of the TA4 gene.

Before polyA RNA could be used as a template for cDNA synthesis, it was necessary to demonstrate the presence of the mRNA encoding the TA4 antigen. The presence of the TA4 antigen mRNA was demonstrated by hybridizing polyA RNA from oocysts at various stages of sporulation with DNA from the clone encoding the TA4 protein. Two micrograms of polyA RNA from each time point during sporulation was electrophoresed through gels containing formaldehyde (25). The RNA was transferred to nitrocellulose filters for Northern blot analysis. Nitrocellulose filters were probed with the 785 bp SacIPvuII fragment of the *E. tenella* genomic clone 108-1 (FIG. 1) which had been nick translated with [$^{32}$P]-dATP (25). The mRNA encoding the TA4 antigen was present approximately 16–20 hours after sporulation was initiated and thereafter (FIG. 3). The time of appearance of the mRNA for the TA4 antigen correlates exactly with the appearance of the 17,000 dalton subunit of the TA4 antigen that is immunoreactive with monoclonal antibody Ptn 9.9 D12 on Western blots. These experiments demonstrate that mRNA from sporulated oocysts could be used to make cDNA encoding the TA4 antigen.

EXAMPLE 4

Isolation and Characterization of a cDNA Clone Encoding the TA4 Antigen cDNA

The nucleotide sequence encoding the TA4 antigen was to be used as a gene in an easily grown cell such as *E. coli* to produce a TA4 protein for vaccination of chickens against coccidiosis caused by certain Eimeria. There are three regions of the TA4 gene (FIG. 1) in which the DNA sequence does not coincide with the protein sequence. These three sequences are introns typically found within the coding regions of many eukaryotic genes. However, since genes containing introns would not express the proper protein in *E. coli* it was necessary to isolate a cDNA clone encoding the TA4 antigen. This clone contains a continuous coding sequence for the TA4 antigen.

Synthesis of cDNA

Briefly, the sporulated oocyst mRNA isolated as described in Example 3 was transcribed into cDNA by the action of AMV reverse transcriptase as described by Ullrich et al. (47). Transcription was initiated at the 3'-polyadenylated end of the TA4 antigen mRNA using oligo-dT as a primer. The second DNA strand was copied using DNA Polymerase I (the Klenow fragment). From 2 micrograms of mRNA we obtained 340 ng cDNA.

Specifically, 2 micrograms of oligo-dT (12–18 nucleotides, Pharmacia Molecular Biology Division, Piscataway, NJ) was annealed to 2 micrograms of purified mRNA in the presence of 50 mM NaCl. The annealing reaction was heated to 90° C. and then slowly cooled. For the reverse transcriptase reaction, deoxynucleosidetriphosphates (A, T, G, C) were added to 0.5 mM along with 40 units of enzyme (Molecular Genetic Resources, Tampa, FL). The reverse transcriptase reaction buffer was as follows: 15 mM Tris-HCl, pH 8.3, 21 mM KCl, 8 mM $MgCl_2$, 0.1 mM EDTA, and 30 mM beta-mercaptoethanol. This mixture was incubated at 42° C. for 45 minutes. The RNA-DNA duplex was extracted once with phenol chloroform and then precipitated with ethanol. The pelleted material was then resuspended in 100 microliters of reaction mixture containing the following: 20 mM Tris-HCl pH 7.5, 5 mM $MgCl_2$, 100 mM KCl and 250 mM each dATP, dCTP, dTTP, dGTP.

RNAse H (100 units/ml Pharmacia Molecular Biology Division, Piscataway, NJ) and DNA Polymerase I-Klenow fragment (50 units/ml Boehringer Mannheim, Indianapolis, IN) were added and the reaction was incubated at 12° C. for 60 minutes. The combined activities of these enzymes result in the displacement of the mRNA from the RNA-DNA duplex as the first cDNA strand is used as a template for synthesis of the second cDNA strand. The reaction was stopped by the addition of EDTA to a final concentration of 10 mM and the DNA duplex was then extracted with phenol:-chloroform and ethanol precipitated. The sequence of the reactions of DNA Polymerase I and RNAse H was predicted to yield cDNA molecules which were blunt ended at both their 3' and 5' ends. A 3' blunt end was necessary for the subsequent cloning of the cDNA.

Construction of the TA4 cDNA Library

The cDNA was resuspended in 100 microliters of sterile water. To clone the cDNA into a library a restriction site was used that had been determined from the genomic clone 108-1 DNA sequence. A SacI site is immediately upstream to the N-terminal glutamine of the mature 17,000 dalton subunit of the TA4 antigen. Approximately 50 ng was digested with SacI (50 units/ml) in the presence of 6 mM Tris-HCl (pH 7.4) 6 mM $MgCl_2$, and 6 mM beta-mercaptoethanol for 60 minutes at 37° C.

The sample was then re-extracted with phenol:-chloroform and ethanol precipitated. For the cloning step a pUC18 vector (32) was used. The vector had been digested with SacI and SmaI. SmaI provided the blunt end site necessary for ligation of the 3' end of the cDNA. The ligation reaction was performed using 40 ng of vector DNA and 50 ng of cDNA. Ligations were done overnight at 12° C. in a ligase buffer of 50 mM Tris-HCl (pH 7.8), 10 mM $MgCl_2$, 20 mM dithiothreitol, 1.0 mM rATP using one unit of T4 DNA ligase.

The recombinant DNA molecules were then introduced into *Escherichia coli* K-12 strain MHl by transformation. The transformed bacteria were spread on agar plates containing the antibiotic ampicillin at a concentration of 50 micrograms/ml. Since the plasmid pUC18 (32) contains the ampicillin resistance gene, only those bacteria which acquired a recombinant plasmid survived. These bacteria each grew and divided to form a bacterial colony. Each cell in the colony is a descendant of the original parental cell and contains the same recombinant plasmid. Approximately 6700 clones were obtained from the 55 nanograms of cDNA used to make recombinant plasmids.

IDENTIFICATION OF TA4 cDNA CLONES

This cDNA library was screened by colony hybridization using the high density screening method described by Grunstein and Hogness (11). The 785 bp SacI-PvuII fragment of the genomic clone was purified and labeled with $^{32}P$ by nick-translation (25). Positive clones were identified, purified and plasmid DNA was isolated for further analysis. Restriction analysis of the positive cDNA clone agreed with the map of the genomic clone. The cDNA insert of the clone designated as pTCD26 was sequenced by dideoxy sequencing using oligonucleotide primers made to correspond to the genomic clone (35). The sequence of the cDNA pTCD26 clone is shown in FIG. 4. This cDNA clone was transformed into an *E. coli* strain JM83, and the strain designated as JM83/pTCD26 was deposited with the American Type Culture Collection, Rockville, MD, and assigned ATCC accession No. 53315. This deposit was made pursuant to the Budapest Treaty On The International Recognition Of The Deposit Of Microorganisms For The Purpose Of Patent Procedure (hereinafter "Budapest Treaty")

The DNA sequence agreed with that predicted from the genomic clone. The predicted amino acid sequence from the cDNA agreed with the TA4 antigen amino acid sequence obtained by protein microsequencing.

EXAMPLE 5

Expression of the cDNA Derived TA4 Antigen Gene in *E. coli*

Contruction of cDNA Derived TA4 Direct Expression Plasmids

The cDNA clone provides the gene for synthesis of the TA4 protein in bacteria. However, the cDNA does not contain the proper signals to allow transcription and translation in *E. coli*. Therefore, the cloned cDNA was inserted into expression vectors that contain a strong promoter(s) for RNA polymerase and a ribosome binding site to initiate protein synthesis in *E. coli* upstream of the inserted cDNA. As used herein, the phrase TA4 protein refers to the expression product of the cDNA of FIG. 4 or any recombinant TA4-derived material produced in a bacterial host cell. The phrase TA4 antigen refers to the naturally-occurring material as expressed by the genomic TA4 DNA, as present on the surface of the sporozoite or purified away from sporozoites.

Expression vectors pWHA33 and pWHA63 were constructed so that genes could be inserted in them to obtain expression in *E. coli*. Other suitable plasmids known to one skilled in the art could also be used. Plasmids pWHA33 and pWHA63 are two examples of suitable plasmids. The pWHA33 plasmid contains three promoters (lac, lambda $P_R$ and trp) each of which could direct transcription of an inserted gene. Plasmids containing various combinations of these promoters and the tac promoter from plasmid pDR450 (34; Pharmacia Molecular Biology Division, Piscataway, NJ) were constructed. The structure of plasmids pWHA33 and pWHA63 are diagramatically shown in FIG. 5.

One strategy to synthesize the TA4 protein in *E. coli* is to simply provide a ribosomal binding site and a methionine codon (ATG) preceding the coding sequence. To construct such a direct expression plasmid for the TA4 protein, the cDNA clone pTCD26 was digested with SacI and then treated with Klenow fragment of DNA polymerase I to produce blunt ends. An oligonucleotide linker COD-154 was ligated to the blunted SacI end to provide the ATG codon to initiate protein synthesis and the BamHI site necessary to clone into the BamHI site of pWHA63. The structure of COD-154 is:

Ribosome Binding Site

CATAAGGATCCTTATG

BamHI site    Start codon

The insertion of TT immediately preceding the initiation codon ATG in COD-154 is to improve efficiency of translational initiation.

After ligation of oligonucleotide COD-154 to the blunt ends of pTCD26, the product was digested with BamHI. The 1276 bp fragment containing the TA4 gene was purified on a polyacrylamide gel and then ligated into the BamHI site of expression vector pWHA63 resulting in plasmid pDET1. The construction of pDET1 is diagramatically shown in FIG. 5. Another direct expression plasmid, pDET2 was constructed from pDET1 by digestion of pDET1 with HindIII and religation which removed the HindIII fragment containing lambda $P_R$ and lambda cI. The pDET1 and pDET2 direct expression vectors were transformed into *E. coli* strain REN3.

The recombinant DNAs and host microorganisms described herein as REN3/pDET1 and REN3/pDET2 were deposited with the American Type Culture Collection, Rockville, MD and assigned ATCC Accession Numbers 53316 and 53318, respectively. These deposits were made pursuant to the Budapest Treaty.

Synthesis and Analysis of Cloned Gene Products in *E. coli*

Lysates of cells containing pDET1 and pDET2 were analyzed for the presence of the TA4 protein. Proteins synthesized by the pDET1 and pDET2 DNA were identified by probing Western blots of cell lysates with mouse antiserum raised against the reduced, denatured 17,000 dalton subunit of the *E. tenella* TA4 antigen.

Expression of pDET1 and pDET2 was analyzed first in *E. coli* strain W3110 (W3110 carries the wild-type Lon+ protease gene). Cultures of W3110/pDET1 and W3110/pDET2 were grown in L-broth (10 g/l tryptone (Difco), 5 g/l yeast extract (Difco), 5 g/l NaCl, adjusted to pH 7.5 with NaOH) supplemented with 100 micrograms/ml ampicillin. To obtain optimum expression, cultures were shaken at 30° C. to a cell density of $1-5\times10^8$/ml, diluted 1:5 into fresh media and shaken at 37° for 2 to 6 hours. Cells were harvested by centrifugation, washed in M9 salts (6 g/l $Na_2HPO_4$, 3 g/l $KH_2PO_4$, 0.5 g/l NaCl, 1 g/l $NH_4Cl$) and resuspended at $5\times10^9$/ml in Laemmli gel sample buffer (18). Twelve microliter samples were heated 10 minutes, 100° C., and run on 12½% SDS-PAGE, and either stained with Coomassie Blue, or transferred to nitrocellulose sheets and probed with a 1:1000 dilution of mouse antiserum to reduced-denatured 17,000 dalton TA4 polypeptide as described above.

Expression of the TA4 gene in pDET1 and pDET2 is very low in *E. coli* strain W3110. The 25,000 dalton TA4 protein is visible only faintly on Western blots and not visible above background on Coomassie Blue stained polyacrylamide gels of total cell lysates, suggesting that net synthesis is less than 0.5% of total *E. coli* protein.

It appeared likely that the apparent low expression of pDET1 and pDET2 was due to instability of the TA4 protein in *E. coli* W3110. Other eukaryotic proteins have been shown to be unstable when synthesized in *E. coli* (9A). therefore, plasmids pDET1 and pDET2 were transformed into *E. coli* strain MTM6, deficient in the lon protease (4). MTM6 is a non-mucoid derivative of Lonstrain AB1899 (CGSC #1899).

Expression of the TA4 gene in pDET1 and pDET2 is greatly increased in strain MTM6 (Lon−). Expression was analyzed as described above for W3110. FIG. 6 compares synthesis of pDET1 in W3110 (Lon+) and MTM6 (Lon−). Strains containing either pDET1 or pDET2 DNA produced a 25,000 dalton polypeptide that is immunoreactive with the mouse serum made against the reduced, denatured *E. tenella* TA4 antigen. These results suggest that whereas the 25,000 dalton protein encoded by the TA4 antigen gene is cleaved in *E. tenella* to a 17,000 dalton and 8,000 dalton polypeptide linked by a disulfide bond, this post-translational processing does not occur in *E. coli.*

When the lysates were separated into soluble and insoluble components by centrifugation, the vast majority of the 25,000 dalton protein was localized in the insoluble fraction of the cell lysate (FIG. 6). This insoluble protein does not appear immunoreactive with monoclonal antibody Ptn 7.2 A4/4 which recognizes the TA4 antigen in sporozoite membranes or extracted from sporozoite membranes without reduction of disulfite bonds.

Because the expression levels of pDET1 and pDET2 are very low in Lon+ *E. coli* and because Lon− *E. coli* might be impractical to grow in large scale cultures, the TA4 protein was stabilized by fusion to other proteins. Any suitable protein could be utilized for this protein fusion. The following examples illustrate only two of the possible proteins which are suitable; namely beta-galactosidase and prochymosin.

EXAMPLE 6

Expression of the TA4 Protein as a Beta-Galactosidase Fusion Protein in *E. coli*

Construction of Beta-Galactosidase-TA4 Expression Plasmids

The observation that the greatest yield of the genetically engineered TA4 protein was obtained in a protease deficient strain suggests that the TA4 protein is subject to degradation in normal *E. coli* cells. TA4 gene fusion plasmids were constructed because attachment of the TA4 protein to a large protein can stabilize it them in *E. coli.* Several eukaryotic proteins are more stable in bacteria as fused proteins (9, 12A). Recombinant plasmid pBGC23 is a hybrid constructed for expression of a beta-galactosidase-TA4 antigen fusion protein. It was derived from a plasmid pDK2 which contains the lac regulatory region and virtually the whole beta-galactosidase gene (1008 codons) from lambda plac (12, 37) inserted into the EcoRI site of plasmid pBR328, and from the cDNA clone pTCD26. The construction of pBGC23 is diagramatically shown in FIG. 7. Suitable plasmids other than pDK2 can also be used. Plasmid pDK2 is one example of a suitable plasmid.

The 1276 bp EcoRI-BamHI fragment from pTCD26 containing the TA4 cDNA sequence was cloned into plasmid pDK2 that had been digested with EcoRI and BamHI to generate plasmid pDK22. Clone pDK22 contained the expected plasmid in which the TA4 cDNA sequence was fused to the C-terminal region of the beta-galactosidase coding sequence. However, in this plasmid the cDNA derived TA4 coding sequence is not in phase with that of beta-galactosidase. Therefore, plasmid pDK22 was digested with EcoRI and then treated with DNA polymerase I Klenow fragment and religated to put the TA4 coding sequences into the proper reading frame. This plasmid, designated pBGC23, contains a hybrid gene that encodes a protein consisting of the TA4 protein fused to the C-terminal region of beta-galactosidase (lacZ). pBGC23 was used to transform *E. coli* strains JM83, and REN3.

The recombinant DNA and its host microorganism described herein as REN3/pBGC23 was deposited with the American Type Culture Collection, Rockville, MD and assigned ATCC Accession Number 53317. This deposit was made pursuant to the Budapest Treaty.

Expression and Analysis of Cloned Gene Products

Proteins encoded by the pBGC23 DNA were identified by probing Western blots of cell lysates with mouse serum against the purified reduced denatured 17,000 dalton subunit of the *E. tenella* TA4 antigen as described in Example 5. JM83/pBGC123 and REN3/pBGC23 were grown in L-broth, supplemented with 0.1% glucose and 100 micrograms/ml amplicillin. Cultures were grown to saturation by shaking at 37° C. overnight. Cells were harvested by centrifugation, washed in M9 salts and resuspended at $5\times10^9$/ml in Laemmli gel sample buffer. 20 microliter samples were heated 10 minutes at 100° C. and run on 7½% SDS-PAGE, and either stained with Coomassie Blue or Western blotted.

Stained and immunoblotted gels (FIG. 8) demonstrated that the expected 135,000 dalton fusion protein is synthesized in JM83/pBGC23 and REN3/pBGC23 cultures but not in JM83 alone. The Western blot shows that the protein is immunoreactive with the mouse serum against the reduced, denatured *E. tenella* TA4 antigen. FIG. 8 shows the protein is present in the insoluble fraction of the cell lysate. Cultures grown as described above were lysed by sonication following lysozyme and EDTA treatment, and cell membranes were solubilized in 2% Triton overnight at 4°. The insoluble material was collected by centrifugation, and the 135,000 dalton pBGC23 product was present in this fraction.

The pBGC23 protein is synthesized in *E. coli* at high levels, but is insoluble and does not react with monoclonal antibody PTn 7.2 A4/4. Furthermore, this insoluble pBGC23 protein, when injected into mice will not raise antibodies that cross-react with native TA4 antigen.

EXAMPLE 7

Expression of the TA4 Protein as a Prochymosin Fusion Protein in *E. coli*

The protein made by cells containing pDET1, pDET2 or pBGC23 are largely or totally insoluble, and thereby are apparently not active with monoclonal antibody Ptn 7.2 A4/4. It was observed tht other eukaryotic proteins that are made in *E. coli* in an insoluble, inactive form can be solubilized and their activity recovered. One such protein is bovine prochymosin. The TA4 cDNA sequence was fused to the bovine prochymosin gene to produce an insoluble fusion protein that could be solubilized and made active by procedures developed for prochymosin alone. The extent of proper renaturation of the fusion protein could then be monitored by following chymosin activity.

A plasmid-encoded prochymosin-TA4 fusion protein was created by joining the TA4 cDNA sequence to the cloned bovine prochymosin gene of pWHA43, which directs synthesis of prochymosin in a stable but insoluble form in *E. coli* (26). Other plasmids may also be utilized. One suitable plasmid is pWHA43.

Figure 9:
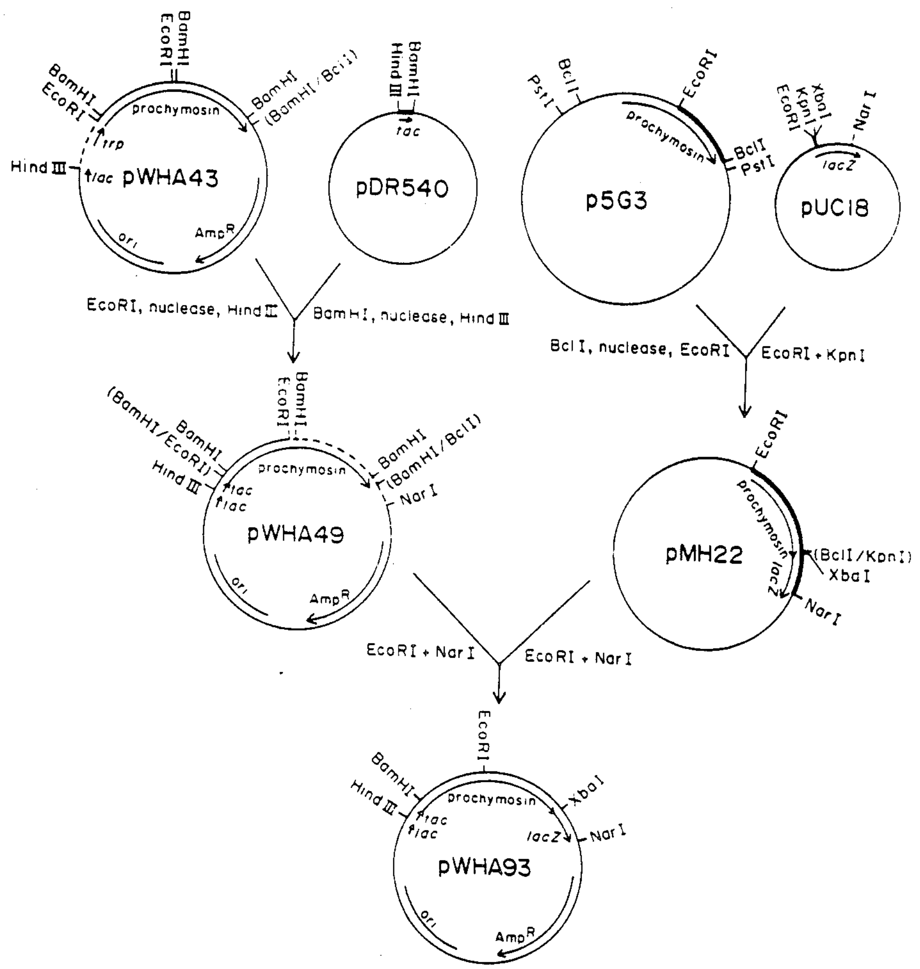
FIG. 9 schematically shows the construction of the bovine prochymosin expression vector pWHA93.

In order to construct the prochymosin-TA4 gene fusion, pWHA43 was converted to pWHA93 as shown in FIG. 9. First, the tac promoter of pDR540 (34) was substituted for the trp promoter to produce pWHA49 by specific restriction endonuclease substitution. Next, the normal stop codon of prochymosin was removed by substituting the C-terminal portion of the prochymosin gene of pWHA49 with a modified prochymosin C-terminal portion from pMH22, to give pWHA93. pMH22 contains the C-terminal half of the gene from the cDNA clone p5G3, fused to the prochymosin BclI site (deleting the stop codon) to the polylinker and beta-galactosidase gene fragment in plasmid pUC18.

In the construction of prochymosin-TA4 gene fusion, pCOC12, a 1294 bp fragment was removed from the cDNA clone pTCD26 by digestion with the enzymes EcoRI and PstI, followed by digestion with Mung bean nuclease to form blunt-ended DNA. The plasmid pWHA93 was digested with XbaI and treated with Mung bean nuclease and the blunt-ended vector was ligated with the blunt-ended fragment containing the TA4 cDNA sequences (1286 bp after Mung bean nuclease treatment) to generate the recombinant plasmid pCOC11. After this ligation, the TA4 derived sequences were found to be out of reading frame with the coding sequences of prochymosin. In order to change the reading frame, pCOC11 was digested with SacI and Mung bean nuclease, and was then religated to generate pCOC12. The construction of pCOC12 is diagrammatically shown in FIG. 10. Plasmid pCOC12 was modified to pCOC14 by removal of two NarI fragments by NarI digestion and religation, reducing the size of the plasmid but not deleting any of the prochymosin or TA4 sequences. Plasmid pCOC14 was modified to form pCOC20 by removal of a 249 bp SphI fragment by digestion with SphI and religation. The 249 nucleotide deletion in the prochymosin sequence of pCOC20 maintains the correct reading frame, and results in an 83 amino acid deletion in the prochymosin portion of the fusion protein.

For expression studies, pCOC12 and pCOC20 were transformed into strain REN3, a bacteriophage T1 resistant derivative of CY15001, a trp R derivative of W3110.

The recombinant DNAs and host microorganisms described herein as REN3/pCOC12 and REN3/-pCOC20 were deposited with the American Type Culture Collection, Rockville, MD and assigned ATCC Accession Numbers 53314 and 53313, respectively. These deposits were made pursuant to the Budapest Treaty.

Expression and Analysis of Cloned Gene Products

Proteins encoded by the pCOC12 and pCOC20 DNAs were identified immunologically, following fractionation by electrophoresis and transfer to nitrocellulose sheets as described in Example 5.

REN3/pCOC12 and REN3/pCOC20 were grown to saturation in L-broth supplemented with 0.1% glucose and 100 micrograms/ml ampicillin by shaking at 30° C. overnight. Cells were harvested by centrifugation, washed in M9 salts and resuspended in Laemmli sample buffer. Samples were heated 10 minutes, 100° C. and run on 10% polyacrylamide gels in SDS and either stained with Coomassie Blue or transferred to nitrocellulose sheets for immunologic analysis, as described.

Triton insoluble material was prepared from REN3/-pCOC12 and REN3/pCOC20 cultures as described in Example 6, and run on polyacrylamide gels.

The stained gels and Western blots shown in FIG. 11 show that pCOC12 DNA encodes a polypeptide of the expected molecular weight, approximately 65,600 daltons that is immunoreactive with the mouse serum against the reduced, denatured *E. tenella* TA4 antigen. As expected, the protein is present in the insoluble fraction of the cell lysate. Plasmid pCOC20 DNA encodes an immunoreactive polypeptide with the expected molecular weight of 56,500. The TA4 protein from pCOC20 is also present in the insoluble fraction of the cell lysate.

EXAMPLE 8

Extration of the TA4 Protein From the Insoluble State and Demonstration of Immunoreactive with Monoclonal Antibody PTN 7.2 A4/4

The *E. coli* products of expression plasmids pDET1, pDET2, pBGC23, pCOC12, pCOC20 are all largely or totally insoluble. All can be solubilized by boiling in Laemmli sample buffer and react with mouse antiserum raised against the 17,000 dalton TA4 antigen subunit. However, none react with monoclonal antibody Ptn 7.2 A4/4 under these conditions. Therefore, it was necessary to solubilize and renature these *E. coli* synthesized proteins to produce antigens in a form that would react with monoclonal antibody Ptn 7.2 A4/4 and therefore could possibly raise neutralizing and protective antibody response against *E. tenella* in animals.

Extraction and Renaturation of Bacterially Produced TA4 Proteins

First the pCOC12 protein was solubilized and renatured by methods known to solubilize and renature bovine prochymosin to produce active enzyme (26). This procedure produced pure soluble pCOC12 protein that possessed both prochymosin activity (milk clotting after acid activation to chymosin) and Ptn 7.2 A4/4 immunoreactivity. Conditions were optimized for recovery of immunoreactivity and are described below.

Plasmid pCOC12 was constructed, as described above, by fusing the 3' end of the coding sequence of bovine prochymosin to the 5' end of the coding sequence of the TA4 polypeptide. This plasmid was used to transform *E. coli* strain REN3 using standard techniques and ampicillin resistant colonies were purified and used for culturing. An ampicillin resistant colony from a freshly streaked agar plate was used to inoculate a 5 ml liquid culture containing L-broth and ampicillin at 100 micrograms/ml. The culture was grown for several hours at 37° C. with shaking until cells had grown to an easily visible turibidity. The 5 ml culture was transferred to a flask containing 1 liter of L-broth/ampicillin supplemented with 0.1% glucose. This culture was grown at 30° C. with shaking to stationary phase. Cells were collected by centrifugation and stored frozen at −70° C. 10 g of frozen cell paste of *E. coli* strain REN3 containing pCOC12 were suspended in 100 ml of 25 mM Tris-HCl pH 8, 10 mM EDTA, 1 mg/ml lysozyme. After a short incubation, the lysed cells were further disrupted by sonication. Prochymosin synthesized in *E. coli* has been shown to be completely insoluble in cell lysates, even in the presence of non-ionic detergents which solubilize cell membranes and membrane proteins. Partial purification of the pCOC12-encoded prochymosin-TA4 fusion protein was achieved by centrifugation of the cell lysate at 10,000×g for ten minutes, followed by an overnight detergent extraction of the pelleted cell debris with a buffer solution containing 2% Triton X-100 detergent (Sigma Chemical Co., St. Louis, MO). The pCOC12 fusion protein remained insoluble and was collected by centrifugation.

This purification was improved slightly by additional washing of the insoluble material with the solution containing 2% Triton X-100. The pCOC12 prochymosin-TA4 protein was suspended in 6.3 or 12.6 ml of 10 mM sodium phosphate buffer at pH 7.5. The suspension is fully solubilized by the addition of solid urea to a final concentration of 6–8M in a volume 20 or 10 ml, respectively, and then mixed for 16 hours at room temperature.

The resultant clear solution was diluted into 100 or 50 volumes, respectively of 10 mM sodium phosphate buffer adjusted to pH 11.0 to achieve a final volume of 1000 mls. The solution was mixed thoroughly and allowed to stand for 20 minutes at 15°–25° C. The pH of the solution was then titrated to pH 8.3 by addition of 0.2N HCl over a period of 3 minutes.

The resultant solution was left at room temperature for one hour or more prior to assay or storage. This solution contained approximately 100 micrograms/ml of the 65,600 dalton protein which was 80–90% pure. The sample was assayed for chymosin enzymatic activity or immunoreactivity with monoclonal antibody Ptn 7.2 A4/4 as detailed below.

Assay of chymosin activity was a convenient way to monitor recovery of properly renatured protein. Recovery of immunoreactivity with Ptn 7.2 A4/4 correlated well with recovery of chymosin activity from pCOC12 protein, as measured by milk-clotting activity following acid activation. Recovery of immunoreactivity of the pCOC12 protein as described below and shown in FIG. 12.

The other TA4 proteins and protein fusions described above were solubilized and renatured by the same or similar methods. Plasmid pCOC20 was constructed, as diagrammed in FIG. 10, by a SphI deletion within the prochymosin component of the pCOC14 fusion protein. This deletion maintained the correct reading frame within the gene fusion and had no effect on the insolubility of subsequent solubilization of renaturation of the pCOC20 fusion protein. While the pCOC20 fusion protein maintained immunoreactivity of its TA4 epitope, the deletion-containing prochymosin domain could not be activated to a form having milk clotting activity. Plasmid pCOC20 was used to transform *E. coli* strain REN3 that was cultured as described above. The insoluble pCOC20 prochymosin-TA4 protein was isolated and renatured from 10 grams of frozen cell paste of REN3/pCOC20 as described above.

Plasmid pGBC23 was constructed, as diagrammed in FIG. 7, by fusing the 3′ end of the coding sequence of *E. coli* beta-galactosidase to the 5′ end of the coding sequence of the cDNA derived TA4 polypeptide. This plasmid was used to transform *E. coli* strain JM83 (cultured as described above). The beta-galactosidase-TA4 fusion polypeptide was found to be insoluble within a cell lysate and was isolated and renatured from 10 gms of frozen cell paste of JM83/pBGC23 by the methods described above. Plasmid pDET2 was constructed, as diagrammed above, so as to express the TA4 protein directly rather than as a fusion polypeptide. Optimal yield of the pDET2 protein was achieved in a protease deficient *E. coli* strain MTM6. This strain was cultured as described above with the following exception. When the 1 liter culture of cells grown at 30° C. reached an optical density of 0.5 (Abs at 600 nm) the temperature was raised to 37° C. for 1 to 2 hours. The cells were harvested and stored frozen at −70° C.

10 grams of frozen cell paste of MTM6/pDET2 were lysed using the methods described above, and the Triton insoluble protein was isolated and dissolved in urea as described above. The solubilized protein was renatured by extensive dialysis against 10 mM sodium phosphte buffer, pH 8.5.

Immunoassay of Renatured Samples

The immunoreactivity of the renatured pCOC12, pCOC20, pDET2 and pBGC23 proteins with monoclonal antibody Ptn 7.2 A4/4 was measured relative to the TA4 antigen purified from *E. tenella* sporocysts. Each well of the microtiter plate (Immulon I micro-ELISA flat-bottom well plates, Dynatech Laboratories, Inc., Alexandria VI) was coated with 100 microliters antigen diluted in 10 mM $Na_2HPO4$, 150 mM NaCl, 0.01% (w/v) Zwittergent TM 3–12, pH 8.0. For renatured samples, 1:10 to 1:1000 dilutions of the antigen were assayed. The purified *E. tenella* antigen was assayed in parallel at concenrations of 0.5–10 ng/well. Plates were coated with the antigens by incubation with the antigen solution for 1 hour at room temperature and then overnight at 4° C. Wells were emptied and then washed three times with phosphate buffered saline pH 7.2 containing 0.02% (v/v) Tween-20 (PBST). The plates were treated with 3% (w/v) gelatin, 10 mM Tris-HCl pH 7.5, 150 mM NaCl, 0.05% (w/v) $NaN_3$ for 30 minutes at room temperature to block any remaining protein binding sites. Plaes were then incubated with 100 microliters of monoclonal antibody Ptn 7.2 A4/4 (30 micrograms/ml in 3% [w/v] bovine serum albumin, 10 mM Tris-HCl pH 7.5, 150 mM NaCl, 0.05% (w/v) $NaN_3$) for 2 hours at room temperature. After rinsing the wells three times with PBST, the bound monoclonal antibody Ptn 7.2 A4/4 was determined using the Vectastain TM ABC Kit for mouse IgG (Vector Laboratories, Inc. Burlingame, CA). Each well of the plate was filled with 100 microliters of biotinylated horse anti-mouse IgG (40 microliters biotinylated anti-mouse antibody, 80 microliters normal horse serum in 10 ml PBST) and incubated 30 minutes at room temperature. Plates were rinsed three times with PBST. Plates were then incubated with 100 microliters/well of Vectastain ® ABC Reagent for 30 minutes at room temperature (80 microliters Avidin DH Reagent A mixed with 80 microliters biotinylated horseradish peroxidase Reagent B in PBST preincubated for 30 minutes before addition to the plates). After five washes with PBST bound horseradish peroxidase was measured by the addition of 100 microliters substrate/well (0.1 mg/ml 2,2′-azino-di-(3-ethyl-benzthiazoline-6sulfonic acid in 50 mM citrate/phosphate buffer pH 5.3, 0.015% (v/v)

hydrogen peroxide). Plates were incubated in the dark at room temperature. The absorbance at 414 nm was measured 10-60 minutes after substrate addition in a Titertek Multiscan TM automatic plate reader (Flow Laboratories, Inc., McClean, VA).

Figure 12:
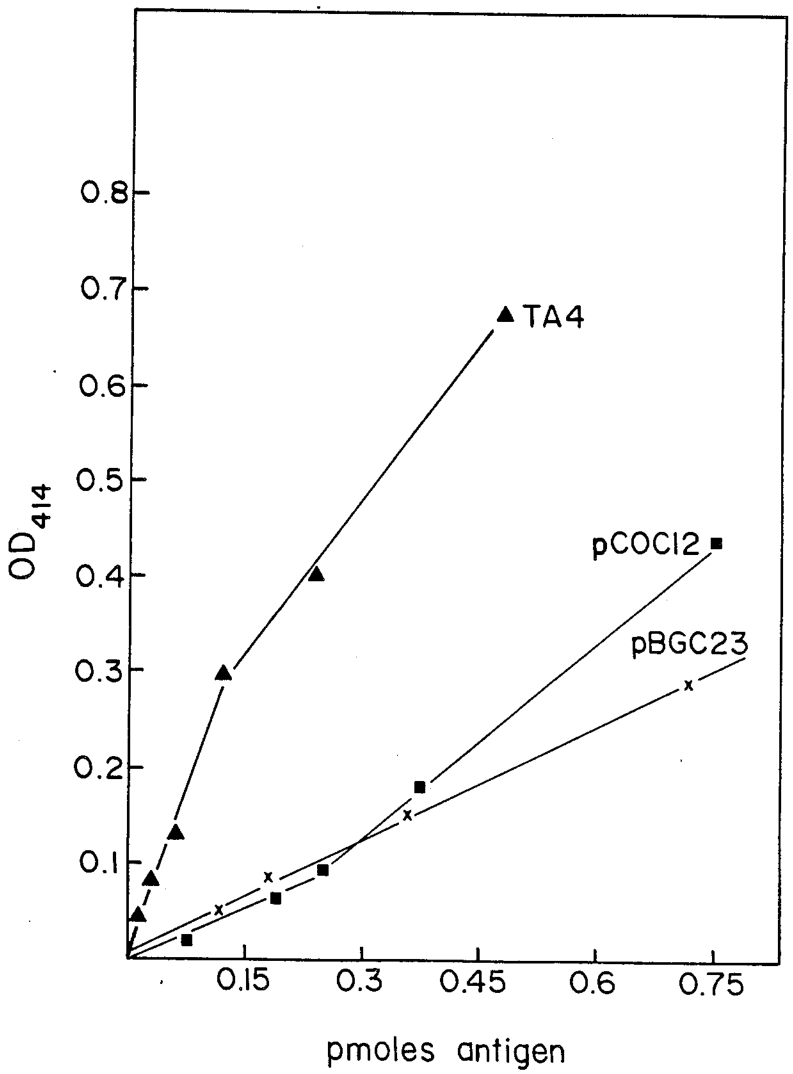
FIG. 12 demonstrates the immunoreactivity of the renatured bacterial TA4 proteins with monoclonal antibody Ptn 7.2 A4/4.

The relative immunoreactivities of the various renatured antigens (e.g., encoded by pBGC23, PCOC12, pCOC20 and pDET2) were compared with that of the TA4 antigen extracted from *E. tenella* oocysts. Increasing amounts of each protein were added to microtiter plate wells and the $OD_{414}$ of the reaction in each well was plotted against the antigen mass present (FIG. 12). The immunoreactivity of the bacterially-produced proteins subjected to the denaturation/renaturation treatment described above range between 10 and 30% of the activity of the *E. tenella*-extracted protein, on a molar equivalent basis.

EXAMPLE 9

Use of Bacterially Produced TA4 Proteins To Raise Serum Antibodies iin Mice That Cross React With the *E. Tenella* TA4 Antigen The immunogencity of bacterially-produced TA4 protein was tested by subcutaneous injections in CB6-F1 mice. Renatured pCOC12 and pBGC23 proteins as well as insoluble proteins from the constructs were tested. Purified *E.tenella* TA4 antigen was used as a positive control and renatured prochymosin (from strain REN3 containing pWHA49) as a negative control. A group of 5 mice was injected for each antigen. Mice were injected twice at a 35 day interval and bled about 10 days after each injection.

For the *E. tenella* TA4 antigen, 10 micrograms was injected subcutaneously per mouse in a mixture of 3 parts antigen solution to 5 parts complete Freund's adjuvant. (Final volume 200 microliters/injection). Renatured pCOC12 and pBGC23 proteins or insoluble proteins from these plasmids were similarly injected at approximately a twofold molar excess of the bacterial TA4 protein as compared to the *E. tenella* antigen.

Sera were assayed by the ELISA method described in Example 8. Microtiter plates were coated with 2 ng of the purified *E. tenella* TA4 antigen/well. The results of the assay with sera from the second bleed are shown in the Table I below.

TABLE I

| Antisera Raised Against | Absorbance-Blank (414 nm)* ($\bar{X}$ ± S.D.) |
|---|---|
| Renatured Prochymosin | 0 |
| Renatured pCOC12 Protein | 0.31 ± 0.06 |
| Insoluble pCOC12 Protein | 0.01 ± 0.01 |
| Renatured pBGC23 Protein | 0.29 ± 0.05 |
| Insoluble pBGC23 Protein | 0.03 ± 0.04 |
| *E. tenella* Purified TA4 | 0.36 ± 0.11 |

*5 mice/group; values for 1:3000 dilution of sera presented.

These experiments indicate that the mice immunized with pCOC12 or pBGC23 proteins that went through the renaturation protocol raised antobodies that cross-react with the purified *E. tenella* TA4 antigen. These sera gave a strong positive signal with the purified *E. tenella* TA4 antigen to at least a 1:3000 dilution. On the other hand, sera from mice injected with insoluble pCOC12 and pBGC23 proteins had essentially no cross-reacting antibodies to the *E. tenella* TA4 antigen even at sera dilutions as low as 1:30. These experiments indicate that the unpurified, non-renatured insoluble pCOC12 and pBGC23 proteins were not effective immunogens.

EXAMPLE 10

Use of Bacterially Produced TA4 Proteins to Elicit Sporozoite Neutralizing Serum Response and Protective Response Against *E. Tenella* in Chickens It has been previously demonstrated that administratin of the TA4 antigen purified from *E. tenella* (15 micrograms) produced serum antibodies that neutralized sporozoites in vitro and protected chickens against an *E. tenella* challenge. The renatured pCOC12 and pBGC23 proteins were tested for both these properties. Betagalactosidase and renatured prochymosin were used as controls. Renatured pBGC23 protein, pCOC12 protein, and prochymosin were concentrated by dialysis against polyethylene glycol or by hollow fiber filtration (cartridge HIPlO-20, Amicon Corp. Danvers, MA) to a final concentration of 0.5-2.0 mg/ml. Each antigen was formulated as one volume of protein concentrate to three volumes of oil carrier consisting of 5% Arlacel, 94% Drakeol 6-VR and 1% Tween 80. The dose of each antigen employed is listed in Table II. The doses chosen contained approximately 0.5-2 times the molar amount of purified *E. tenella* native TA4 antigen previously shown to be effective in evoking an immune response.

TABLE II

| ANTIGEN | MICROGRAMS/DOSE |
|---|---|
| Beta-galactosidase | 133 |
| Renatured pBGC23 Protein | 80 |
| Renatured pBGC23 Protein | 160 |
| Renatured Prochymosin | 53 |
| Renatured pCOC12 Protein | 80 |

In experiment 1, chickens received 0.2-0.55 cc of the appropriately formulated vaccine by intramuscular injection in the neck. Chickens received booster vaccinations by the same route two additional times separated by two-week intervals. In experiment 2, chickens received 0.2-0.45 cc of the appropriately formulated vaccine by injection into duodenal tissue. Chickens received one booster vaccination by the same route two weeks later. Three days prior to each administration of protein and eleven days after the final administration birds were bled for collection of serum samples.

Eliciting Sporozoite Neutralizing Serum Response Against *E. tenella*

Heat-inactivated sera from chickens in Experiments 1 and 2 were tested for neutralization of *E. tenella* sporozoites. The microneutralization assay was performed with primary chick kidney cell cultures as follows. One to two-week old chicks were sacrificed and asceptically nephrectomized. The kidneys were trypsinized, and cells plated into 96 well cultures at a density of approximately $10^4$/well in Earles LAH medium supplemented with 5% heat-inactivated fetal calf serum. Cultures were maintained at 41° C. in a 5% $CO_2$ atmosphere. When cell cultures reached a level of approximately 50% confluency, 50 microliters of appropriately diluted test serum was added to each well of the plate. Next, $2\text{-}3\times10^4$ sporozoites in 50 microliters of Earles culture medium were added to all wells of the plate. Twelve to sixteen hours later, the culture supernatant was replaced with fresh Earle LAH containing 2% heat inactivated fetal calf serum. The cultures were terminated at 40-44 hours post-infection. Culture supernatants were emptied from the plates at that time. Subsequently, cells were fixed to the plates by the addition of methanol, acidified with 5% glacial acetic acid. The fixed cultures were stained with 0.1% toluidine blue before examining. Wells were scored as to the approximate percentage of inhibition of schizogony. Neutralization of parasites was scored on the basis of the maximum serum dilution still producing complete inhibition of schizont development.

The results in Table III indicate that whereas birds vaccinated with beta-galactosidase or renatured prochymosin had no demonstrable neutralizing antiserum titers against *E. tenella* sporozoites, birds receiving three doses of pBGC23 protein or pCOC12 protein intramuscularly had demonstrable neutralizing antiserum titers.

TABLE III

| Serum Sample | | Geometric Mean Sporozoite Neutralizing Titers |
|---|---|---|
| Experiment 1 | Pre-bleed IM | <1:2.0 |
| | Adjuvant Only | <1:2.0 |
| | Beta-galactosidase | <1:2.0 |
| | Renatured pBGC23 Protein (80 micrograms) | 1:3.2 |
| | Renatured pBGC23 Protein (160 micrograms) | 1:2.6 |
| | Renatured Prochymosin | <1:2.0 |
| | Renatured pCOC12 Protein | 1:4.0 |
| | Sporozoite Immune | 1:16.0 |

Demonstration that Neutralizing Serum of Chickens Immunized with *E. coli*-Produced TA4 Protein Compete with Monoclonal Antibody Ptn 7.2 A4/4

Sera from vaccinated birds with demonstrable neutralization titers to *E. tenella* sporozoites, as well as corresponding control sera were tested for the ability to compete with antibody Ptn 7.2 A4/4 for binding sites on sporozoite membranes. Polystyrene 96 well plates (Immulon II) were incubated with 50 microliters of sporozoite membrane proteins in 10 mM glycine buffered saline, pH 9.6, at a level of approximately 100 micrograms total protein/ml overnight at 37° C. After washing plates three times with PBS-Tween (0.05% Tween-20) plates were incubated for 1 hour with 3% (w/v) bovine serum albumin (RIA grade, Sigma Chemical Co., St. Louis, MO) in PBS. Serial two-fold dilutions of sera from 1:2 to 1:200 were prepared in 0.15M phosphate buffered saline with 0.0005% Tween-20 and incubated with the plates for 3 hours at 37° C. Plates were then incubated with alkaline phosphatase conjugated Ptn 7.2 A4/4 monoclonal antibody for 1 hour at 37° C. The plates were rinsed free of unreacted materials using 0.15M phosphate buffered saline with (0.0005%) Tween-20. Afterward, 100 microliters of substrate solution consisting of 1 mg/ml sodium p-phosphonitrophenol in 1M diethanolamine buffer was added to each well. The resultant reaction product was monitored spectrophometrically. Sera from birds responding to the parenteral vaccination program, as evidenced by neutralization of sporozoites, contained antibody which competed with monoclonal antibody Ptn 7.2 A4/4 (Table IV). This experiment provided direct evidence that renatured pBGC23 and pCOC12 proteins were capable of stimulating an immune response in chickens to a region of the TA4 antigen recognized by monoclonal antibody Ptn 7.2 A4/4.

TABLE IV

| Ptn 7.2 A4/4 Competition titers (50% Inhibition) | |
|---|---|
| Experiment 1 | Reciprocal Titer |
| Pre-bleed | 0 |
| Beta-galactosidase | 0 |
| Renatured pBGC23 Protein (80 micrograms) | 6.5 |
| Renatured pBGC23 Protein (160 micrograms) | 6.5 |
| Renatured Prochymosin | 0.6 |
| Renatured pCOC12 Protein (80 micrograms) | 13.1 |
| Renatured pCOC12 Protein (40 micrograms) | 9.9 |
| Native TA4 | 14.6 |

Immunization with Various TA4 Proteins Reduced the Severity of Infection in Chickens Challenged with *E. tenella*

Eleven days after the last vaccination, chickens were challenged with a low level of coccidia (ca. 300–500 oocysts) and maintained in floor pens. The bedding was not removed so as to maximize oocyst recycling. Chickens received a second challenge of 4000–5000 oocysts one week after the primary challenge to maximize uniformity of lesion development. Chickens were sacrificed 6 days later for evaluation of lesion development. Lesion scores were assessed by the parameters established by Johnson and Reid (15).

The results in Table V demonstrate that birds vaccinated with renatured pBGC23 or pCOC12 protein developed less severe lesions following challenge than did the corresponding control groups. Vaccination with either renatured pBGC23 or pCOC12 protein not only abolished the development of the most severe lesions (level=4) but also shifted the distribution of lesion severity to lower values. Approximately 50–70% of vaccinated birds registered lesions of 1–2 whereas 50–70% of the control birds had lesion scores of 3–4.

TABLE V

| Treatment | % Distribution Lesion Scores | | | | |
|---|---|---|---|---|---|
| | 0 | 1 | 2 | 3 | 4 |
| Experiment 1 | | | | | |
| Beta-galactosidase | 0 | 0 | 22.2 | 50.0 | 27.8 |
| Renatured pBGC23 Protein (80 micrograms) | 0 | 13.8 | 38.5 | 61.5 | 0 |
| Renatured pBGC23 Protein (160 micrograms) | 0 | 30.8 | 38.5 | 30.8 | 0 |
| Renatured Prochymosin | 0 | 7.1 | 21.4 | 57.1 | 14.3 |
| Renatured pCOC12 Protein | 0 | 11.1 | 44.4 | 44.4 | 0 |
| Nonvaccinated Control | 0 | 0 | 12.5 | 68.5 | 18.8 |
| Experiment 2 | | | | | |
| Beta-galactosidase | 0 | 8 | 27 | 37 | 28 |
| Renatured pBGC23 Protein (160 micrograms) | 0 | 34 | 44 | 22 | 0 |
| Renatured Prochymosin | 0 | 0 | 29 | 29 | 42 |
| Renatured pCOC12 Protein | 0 | 42 | 14 | 14 | 30 |
| Nonvaccinated Control | 0 | 0 | 0 | 20 | 80 |

REFERENCES

1. Ali, N. S., Binnerts, W. T. and Klimes, B. (1972). Immunization by (sic) irradiated *Eimeria acervulina.* J. Prot. 19, 177.

2. Aviv, H. and Leder, P. (1972). Purification of biologically active globin messenger RNA by chromatography on oligothymidylic acid cellulose. Proc. Natl. Acad. Sci. 69, 1408.

3. Burnett, W. N. (1981). "Western Blotting": electrophoretic transfer of proteins from sodium dodecylsulfate-polyacrylamide gels to unmodified nitrocellulose and radiographic detection with antibody and radioiodinated protein A. Anal. Biochem. 112, 195.

4. Chung, C. H. and Goldberg, A. L. (1981). The product of the ion (capR) gene in *Escherichia coli* is the ATP dependent protease, Protease La. Proc. Natl. Acad. Sci. USA 78, 4931.

5. Danforth, H. D. (1982). Development of hybridoma-produced antibodies directed against *Eimeria tenella* and *E. mitis.* J. Parasitol. 68, 392.

6. Danforth, H. D. (1983). Use of monoclonal antibodies directed against *Eimeria tenella* sporozoites to determine stage specificity and in vitro effect on parasite penetration and development. Am. J. Vet. Res. 44, 1722.

7. Danforth, H. D. and Augustine P. C. (1983). Specificity and cross-reactivity of immune serum and hybridoma antibodies to various species of avian coccidia. Poultry Science 62, 2145.

8. Giambrone, J. J., Klesius, P. H. and Edgar, S. A. (1980). Avian Coccidiosis: Evidence for a cell-mediated immune response. Poultry Science 59, 38.

9. Goeddel, D. V., Kleid, D. G., Bolivar, F., Heyneker, H. L., Yansura, D. G., Crea, R., Hirose, T., Kraszewski, A., Itakura, K. and Riggs, A. D. (1979). Expression in *Escherichia coli* of chemically synthesized genes for human insulin. Proc. Nat. Acad. Sci. USA 76, 106–110.

9.A. Goff, S. A. And Goldberg, A. L. (1985). Production of Abnormal Proteins in *E. coli* Stimulates Transcription of lon and Other Heat Shock Genes. Cell 41, 587–595.

10. Gore, T. C., Long, P. L., Kogut, M. and Johnson, J. (1983). Attenuation of *Eimeria necatrix* and *E. tenella* of U.S. origin by serial embryo passage. Avian Disease 27, 569.

11. Grunstein, M. and Hogness, D. S. (1975). Colony hybridization: A method for the isolation of cloned DNAs that contain a specific gene. Proc. Natl. Acad. Sci. USA 72, 3961.

12. Helling, R. B., Goodman, H. M. and Boyer, H. W. (1974) Analysis of Endonuclease EcoRI Fragments of DNA from Lamboid Bacteriophages and other viruses by agarose gel electrophoresis. J. Virol. 14, 1235–1244.

12.A. Itakura, K., Hirose, T., Crea, R., Riggs, A. D., Heynechker, H. L., Bolivar, F. and Boyer, H. W. (1977). Expression in *Escherichia coli* of a chemically synthesized gene for the hormone somatostatin. Science 198, 1056–1063.

13. Jeffers, T. K. (1975). Attenuation of *Eimeria tenella* through selection for precociousness. J. Parasitol. 61, 1083.

14. Jeffers, T. K. (1976). Genetic recombination of precociousness and anticoccidial drug resistance on *Eimeria tenella.* Zeitschrift fur Parasitenkunde 50, 251.

15. Johnson, J. and Reid, W. M. (1970). Anticoccidial Drugs: Lesion scoring techniques in battery and floor pen experiments with chickens. Exp. Parasitology 38, 36.

16. Kasper, L. H., Crabb, J. H., and Pfefferkorn, E. R. (1983). Purification of a major membrane protein of *Toxoplasma gondii* by immunoabsorption with a monoclonal antibody. J. Immunol. 130, 2407.

17. Kleid D. G., Yansura, D., Small, B., Dowbenko, D., Moore, D. M., Grubman, M. J., McKercher, P. D., Morgan, D. O., Robertson, B. H. and Bachrach, H. L. (1981). Cloned viral protein vaccine for foot and mouth disease: responses in cattle and swine. Science 214, 1125.

18. Laemmli, U. K. (1970). Cleavage of structural protein during the assembly of the head of bacteriophage T4, Nature 227, 680.

19. Long, P. L. (1972). *Eimeria mivati:* Reproduction, pathogenicity and immunogenicity of a strain maintained in chick embryos by serial passage. J. Comp. Pathol. 82, 839.

20. Long, P. L. (1974). Further studies on the pathogenicity and immunogenicity of an embryo adapted strain of *Eimeria tenella.* Avian Pathology 3, 255.

21. Long, P. L. (1982). *The Biology of the Coccidia.* University Park Press, Baltimore. Pg. 44.

22. Long, P. L. Johnson, J., and Gore, T. C. (1982). Attenuation of a strain of *Eimeria mivati* of U.S. origin by serial embryo passage. Avian Diseases. 26, 305.

23. Long, P. L. and Rose, M. E. (1965). Active and passive immunization of chickens against induced infections of *Eimeria tenella.* Exp. Parasit. 16, 1.

24. Lowder, L. J. (1966). Artificial acquired immunity to *Eimeria bovis* infections in cattle. Proc. Int. Congr. Parasit. 1, 106.

26. Maniatis, T., Fritsch, E. F. and Sambrook, J. (1982). *Molecular Cloning—A Laboratory Manual,* Cold Springs Harbor Laboratory, New York.

26. McCaman, M. T., Andrews, W. H. and Files, J. G. (1985). Enzymatic properties and processing of bovine prochymosin synthesized in *Escherichia coli.* J. Biotech. 2, 177.

27. McDonald, V. and Ballingall, S. (1982). Further investigation of the pathogenicity, immunogenicity and stability of precocious *Eimeria acervulina.* Parasitology 86, 361.

28. McDonald, V. and Ballingall, S. (1983). Attenuation of *Eimeria mivati* (: mitis) by selection for precocious development. Parasitology 86, 371.

29. McDonald, V., Ballingall, S. and Shirley, M. W. (1982). A preliminary study of the nature of infection and immunity in chickens given an attenuated line of *Eimeria acervulina.* Parasitology 84, 21.

30. McDougald, L. R. Status of coccidiosis: new products on way. Poult. Digest. October, 1981.

31. McDougald, L. R. New anticoccidial drugs: Better things to come or "endangered species?" Feedstuffs Aug. 15, 1983.

32. Norrander, J., Kempe, T. and Messing, J. (1983). Construction of improved M13 vectors using oligodeoxynucleotide-directed mutagenesis. Gene 26, 101.

33. Riley, J. F. (1980). Screening for and evaluation of anticoccidial activity. Adv. Pharm. Chemo. 17, 1.

34. Russell, D. R. and Bennett, G. N. (1982). Construction and analysis of in vivo activity of *E. coli* promoter hybrids and promoter mutants that alter the −35 to −10 spacing. Gene 20, 231–243.

35. Sanger, F. and Coulson, A. R. (1978). The use of thin polyacrylamide gels for DNA sequencing. FEBS Lett. 87, 107.

36. Schmidt, G. O. and Roberts, L. S. (1977). *Foundations of Parasitology.* Mosby Co., St. Louis, pp. 122–128.

37. Shapiro, J., MachHattie, L., Eron, L., Ihler, G., Ippen, K. Beckwith, J. Arditti, R., Reznikoff, W., and MacGillivray, R. (1969). The isolation of pure lac operon DNA. Nature 224, 768–774.

38. Shire, S. J., Bock, L., Ogez, J. Builder, S., Kleid, D. and Moore, D. M. (1984). Purification and immunogenicity of fusion VP1 protein of foot and mouth disease virus. Biochemistry 23, 6474.

39. Shirley, M. W. (1980) *Eimeria necatrix:* The development and characteristics of an egg-shaped (attenuated) line. Parasitology 81, 525.

40. Shirley, M. W. (1982). Features of an attenuated line of *Eimeria praecox.* Parasitology. Proceedings of the British Soc. for Parasitology 81, 525.

41. Shirley, M. W., Bellatti, M. A. and Millard, B. J. (1982). An egg-shaped (attenuated) line of *Eimeria necatrix:* further studies on its reproduction pathogenicity and immunogenicity. Parasitology 84, 215.

42. Speer, C. A., Wong, R. B. and Schenkel, R. H. (1983). Effects of monoclonal IgG antibodies on *Eimeria tenella* (coccidia) sporozoites. J. Parasitol. 69, 775.

43. Speer, C. A., Wong, R. B. and Schenkel, R. H. (983). Ultrastructural localization of monoclonal IgG antibodies for antigenic sites of *Eimeria tenella* oocysts, sporocysts and sporozoites, J. Protozool. 30, 548.

44. Stotish, R. L., Wang, C. C., Hichens, M., VandenHeuvel, W. J. A. and Gale, P. (1976). Studies of a glycoprotein in the oocysts of *Eimeria tenella.* J. Biol. Chem. 251, 302.

45. Stotish, R. L. Profous-Juichelka, H. and Dulski, P. M. (1985). Isolation and in vitro translation of mRNA from *Eimeria tenella.* Fed. Proc. 44, 1334.

46. Towbin, H., Staehelin, T. and Gordon, J. (1979). Electrophoretic transfer of proteins from polyacrylamide gels to nitrocellulose sheets: Procedure and some applications. Proc. Natl. Acad. Sci. USA 76, 4350.

47. Ullrich, A. J., Shine, J., Chirgwin, J., Pictec, R., Tischer, E., Rutter, W. J. and Goodman, H. M. (1977). Rat insulin genes: Construction of plasmids containing the coding sequences. Science 196, 1313.

48. Wang, C. C. (1976). Inhibition of the respiration of *Eimeria tenella* by Quinoline Coccidiostats. Biochem. Pharmacol. 25, 343.

49. Wang, C. C. Biochemistry and physiology of Coccidia. In *The Biology of the Coccidia,* Long, P. L., ed., (1982). University Park Press, Baltimore, pp. 167–228.

50. Wang, C. C. and Stotish, R. L. (1975). Changes in nucleic acids and proteins in the oocysts of *Eimeria tenella* during sporulation. J. Protozool. 22(3), 438.

51. Wisher, M. H. (1983). Sporozoite antigens of Coccidia. J. Cellular Biochem., Supp. 7A, Abstract 0059.

52. Wong, R. B. and Schenkel, R. H. (1984). Monoclonal antibodies analysis of *Eimeria tenella* sporozoite antigens. Fed. Proc. 43(6), 1630.

53. Wright, I. G., White, M., Tracey-Patte, P. D., Donaldson, R. A., Goodger, B. V., Waltisbuhl, O. J. and Mahoney, D. P. (1983). *Babesia bovis:* Isolation of a protective antigen by using monoclonal antibody. Infection and Immunity 41, 244.

What is claimed is:

1. An isolated genomic DNA molecule having the mucleic acid sequence set forth in FIG. 1 and encoding an antigenic protein derived from *Eimeria tenella,* the protein having a molecular weight of about 25,000 daltons and being composed of two polypeptides joined by a disulfide bond, one of the polypeptides being characterized by a molecular weight of about 17,000 daltons and by a blocked N-terminal amino acid and having the amino acid sequence set forth in FIG. 1 and the other of the polypeptides being characterized by a molecular weight of about 8,000 daltons and having the amino acid sequence set forth in FIG. 1.

2. A nucleic acid molecule encoding an antigenic polypeptide, the polypeptide having a molecular weight of about 25,000 daltons and having the continuous amino acid sequence set forth in FIG. 4.

3. A cDNA molecule of claim 2.

4. A mRNA molecule of claim 2.

5. A recombinant cloning vehicle which comprises cloning vehicle DNA and the cDNA of claim 3, the cloning vehicle DNA being characterized by the presence of a first and a second restriction enzyme site and the cDNA being cloned into said sites.

6. A bacterial host cell which comprises the cloning vehicle of claim 5.

7. An *E. coli* host cell of claim 6 designated JM83/pTCD26 and having ATCC accession No. 53315.

8. An expression vector capable of expressing a 25,000 dalton antigenic protein when introduced into a suitable host cell, which comprises suitable carrier DNA and the genomic DNA of claim 1.

9. A bacterial expression vector capable of expressing a 25,000 dalton antigenic polypeptide when introduced into a suitable bacterial host cell, which comprises plasmid DNA and the cDNA of claim 3.

10. The vector of claim 9 designated pDET1.

11. The vector of claim 9 designated pDET2.

12. A vector of claim 9 wherein the plasmid DNA comprises a double-stranded DNA molecule which includes in 5′ and 3′ order the following:

- a DNA sequence which contains either a promoter or a promoter and operator;
- a DNA sequence which contains a ribosomal binding site for rendering the mRNA of the desired gene capable of binding to ribosomes within the host cell
- an ATG initiation codon;
- a restriction enzyme site for inserting a desired gene into the vector in phase with the ATG initiation codon;
- a DNA sequence which contains an origin of replication from a bacterial plasmid capable of autonomous replication in the host cell; and
- a DNA sequence which contains a gene associated with a selectable or identifiable phenotype trait and which is manifested when the vector is present in the host cell.

13. A bacterial expression vector capable of expressing a fused polypeptide having a molecular weight of about 135,000 daltons and being composed of a 25,000 dalton polypeptide fused to beta-galactosidase, which comprises plasmid DNA, DNA of claim 2 and DNA encoding beta-galactosidase.

14. The vector of claim 13 designated pBGC23.

15. A bacterial expression vector capable of expressing a fused polypeptide having a molecular weight of about 65,600 daltons and being composed of a 25,000 dalton polypeptide fused to prochymosin, which comprises plasmid DNA, DNA of claim 2 and DNA encoding prochymosin.

16. The vector of claim 15 designated pCOC12.

17. A bacterial expression vector capable of expressing a fused polypeptide having a molecular weight of about 56,500 daltons and being composed of a 25,000 dalton polypeptide fused to prochymosin which comprises plasmid DNA, DNA of claim 2 and DNA encoding prochymosin which has been modified by SphI digestion resulting in a 249 base pair deletion.

18. The vector of claim 17 designated pCOC20.

19. A host cell which comprises the expression vector of claim 8.

20. A host cell which comprises the expression vector of claim 9.

21. An *E. coli* host cell of claim 20.

22. An *E. coli* host cell designated REN3/pBGC23 which comprises the vector pBGC23 and has ATCC accession No. 53317.

23. An *E. coli* host cell designated REN3/pCOC12, which comprises the vector pCOC12 and has ATCC accession No. 53314.

24. An *E. coli* host cell designated REN3/pCOC20, which comprises the vector pCOC20 and has ATCC accession No. 53313.

25. An *E. coli* host cell designated REN3/pDET1, which comprises the vector pDET1 and has ATCC accession No. 53316.

26. An *E. coli* host cell designated REN3/pDET2, which comprises the vector pDET2 and has ATCC accession No. 53318.

* * * * *